(12) United States Patent
Hwang et al.

(10) Patent No.: US 7,998,682 B2
(45) Date of Patent: Aug. 16, 2011

(54) METHOD FOR ASSESSING ATHEROSCLEROSIS BY MEASURING EXPRESSION OF FOS OR DUSP1 IN MONOCYTES

(75) Inventors: Paul M. Hwang, Rockville, MD (US); Willmar D. Patino, Rockville, MD (US); Omar Y. Mian, Ashburn, VA (US); Ju-Gyeong Kang, Potomac, MD (US); Satoaki Matoba, Rockville, MD (US)

(73) Assignee: The United States of America as represented by the Secretary of the Department of Health and Human Services, Washington, DC (US)

( * ) Notice: Subject to any disclaimer, the term of this patent is extended or adjusted under 35 U.S.C. 154(b) by 1147 days.

(21) Appl. No.: 11/661,714

(22) PCT Filed: Sep. 2, 2005

(86) PCT No.: PCT/US2005/031469
§ 371 (c)(1),
(2), (4) Date: Feb. 27, 2007

(87) PCT Pub. No.: WO2006/029052
PCT Pub. Date: Mar. 16, 2006

(65) Prior Publication Data
US 2007/0258902 A1    Nov. 8, 2007

Related U.S. Application Data

(60) Provisional application No. 60/607,031, filed on Sep. 3, 2004, provisional application No. 60/618,275, filed on Oct. 12, 2004.

(51) Int. Cl.
*G01N 33/53* (2006.01)
*C12Q 1/68* (2006.01)
*C07K 14/47* (2006.01)
*C07K 16/00* (2006.01)
*C07H 21/00* (2006.01)

(52) U.S. Cl. .......... 435/7.1; 435/6; 530/350; 530/387.9; 536/23.5

(58) Field of Classification Search .................. None
See application file for complete search history.

(56) References Cited

FOREIGN PATENT DOCUMENTS
WO    WO 2004/054428    7/2004

OTHER PUBLICATIONS

Zhao et al, 2007. Arteriocler Thromb Vasc Biol. 27: 886-892 plus supplementary materials; 35 pages as printed.*

(Continued)

*Primary Examiner* — Bridget E Bunner
*Assistant Examiner* — Zachary Howard
(74) *Attorney, Agent, or Firm* — Klarquist Sparkman, LLP

(57) ABSTRACT

A non-invasive method for the diagnosis of atherosclerosis is provided. In one example, the method includes assaying the expression of FOS, DUSP1, or both FOS and DUSP1 in monocytes or a cell fraction thereof, or in plasma, serum or peripheral blood from the subject. An increase the expression of FOS, DUSP1, or both FOS and DUSP1 in monocytes in the sample as compared to a control indicates that the subject has atherosclerosis. A method is also provided for determining if a pharmaceutical agent is effective for treatment of atherosclerosis in a subject. The method includes assaying the expression of FOS, DUSP1, or both FOS and DUSP1 in a monocytes treated with the pharmaceutical agent, wherein a decrease the expression of FOS, DUSP1, or both FOS and DUSP1 in monocytes in the sample as compared to a control indicates that the pharmaceutical agent is effective for the treatment of atherosclerosis. The monocytes can be contacted with the agent in vivo or in vitro.

30 Claims, 13 Drawing Sheets

OTHER PUBLICATIONS

Rossner et al, 2004. Mutation Research; pp. 55-63.*

Davis et al., "Fc receptor homologs: newest members of a remarkably diverse Fc receptor gene family," *Immunological Reviews* 190:123-136, 2002.

Davis et al., "Identification of a family of Fc receptor homologs with preferential B cell expression," *PNAS* 98(17):9772-9777, Aug. 14, 2001.

Dichtl et al., "The Carboxyl-Terminal Fragment of α1-Antitrypsin is Present in Atherosclerotic Plaques and Regulates Inflammatory Transcription Factors in Primary Human Monocytes," *Molecular Cell Biology Research Communications* 4:50-61 (2000).

Goetze et al., "TNFα induces expression of transcription factors c-fox, Egr-1, and Ets-1 in vascular lesions through extracellular signal-regulated kinases ½." *Atherosclerosis* 159(1):93-101, Nov. 2001.

Hashimoto et al., "Serial Analysis of Gene Expression in Human Monocytes and Macrophages," *Blood* 94(3):837-844, Aug. 1, 1998.

Küster et al., "Identifying proteins and post-translational modifications by mass spectrometry," *Current Opinion in Structural Biology* 8:393-400, 1998.

Lavezzi et al., "Expression of c-fos, p53 and PCNA in the unstable atherosclerotic arotid plaque," *Int. J. Cardio.* 92(1):59-63, Nov. 2003.

Martínez-González et al., "Biología cellular y molecular de las lesions ateroscleróticas," *Rev Esp Cardiol* 54:218-231, 2001 (*English Abstract*).

Patino et al., "Circulating transcriptome reveals markers of atheroscleorosis," *PNAS* 102(9):3423-3428, Mar. 1, 2005.

Patino et al., "Serial Analysis of Gene Expression: Technical Considerations and Applications to Cardiovascular Biology," *Clinical Research* 91:565-569, 2002.

Rivard et al., "Age-dependent increase in c-fos activity and cylin A expression in vascular smooth muscle cells. A potential link between aging, smooth muscle cell proliferation and atherosclerosis," *Cardiovasc Res* 45(4):1026-1034, Mar. 2000.

Sartippour et al., "Stimulatory Effect of Glucose on Macrophage Lipoprotein Lipase Expression and Production," *Diabetes* 47:431-438, Mar. 1998.

Suzuki et al., "Comprehensive gene expression profile of LPS-stimulated human monocytes by SAGE," *Blood* 96(7):2584-2591, Oct. 1, 2000.

Zhukov et al., "From Isolation to Identification," *PharmaGenomics* p. 18-28, Mar./Apr. 2002.

1st Annual Symposium of the American Heart Association's Council on Basic Cardiovascular Sciences: Stress Signals, Molecular Targets, and the Genome, found at http://www.americanheart.org/presenter.jhtml?identifier=3014865, printed Jul. 23, 2004.

* cited by examiner

SEQUENCE LISTING

<160> NUMBER OF SEQ ID NOS: 45

<210> SEQ ID NO 1
<211> LENGTH: 19
<212> TYPE: DNA
<213> ORGANISM: Homo sapiens

<400> SEQUENCE: 1
catctctgcc ccctctgct                                              19

<210> SEQ ID NO 2
<211> LENGTH: 19
<212> TYPE: DNA
<213> ORGANISM: Homo sapiens

<400> SEQUENCE: 2
acgcctgctt caccaccctt                                             19

```
<210> SEQ ID NO 3
<211> LENGTH: 21
<212> TYPE: DNA
<213> ORGANISM: Homo sapiens

<400> SEQUENCE: 3
gacacaagtc tccagaacgg c                                                 21

<210> SEQ ID NO 4
<211> LENGTH: 21
<212> TYPE: DNA
<213> ORGANISM: Homo sapiens

<400> SEQUENCE: 4
tggtctcaaa gtcatcggga a                                                 21

<210> SEQ ID NO 5
<211> LENGTH: 22
<212> TYPE: DNA
<213> ORGANISM: Homo sapiens

<400> SEQUENCE: 5
ggaggacctt atctgtgcgt ga                                                22

<210> SEQ ID NO 6
<211> LENGTH: 24
<212> TYPE: DNA
<213> ORGANISM: Homo sapiens

<400> SEQUENCE: 6
gaacacacta ttgccaggaa caca                                              24

<210> SEQ ID NO 7
<211> LENGTH: 21
<212> TYPE: DNA
<213> ORGANISM: Homo sapiens

<400> SEQUENCE: 7
ggaggacaac cacaaggcag a                                                 21

<210> SEQ ID NO 8
<211> LENGTH: 24
<212> TYPE: DNA
<213> ORGANISM: Homo sapiens

<400> SEQUENCE: 8
tgtgtcgtcg ggaataatac tggt                                              24

<210> SEQ ID NO 9
<211> LENGTH: 24
<212> TYPE: DNA
<213> ORGANISM: Homo sapiens

<400> SEQUENCE: 9
tgtgtcgtcg ggaataatac tggt                                              24

<210> SEQ ID NO 10
<211> LENGTH: 21
<212> TYPE: DNA
<213> ORGANISM: Homo sapiens

<400> SEQUENCE: 10
ttcaggatgg agtggaggtg c                                                 21
```

```
<210> SEQ ID NO 11
<211> LENGTH: 22
<212> TYPE: DNA
<213> ORGANISM: Homo sapiens

<400> SEQUENCE: 11
cccagaacaa gaaggtgagc aa                                             22

<210> SEQ ID NO 12
<211> LENGTH: 24
<212> TYPE: DNA
<213> ORGANISM: Homo sapiens

<400> SEQUENCE: 12
caagtaagag aacaccctgg gaag                                           24

<210> SEQ ID NO 13
<211> LENGTH: 23
<212> TYPE: DNA
<213> ORGANISM: Homo sapiens

<400> SEQUENCE: 13
tccagtccag ccttacctac agc                                            23

<210> SEQ ID NO 14
<211> LENGTH: 24
<212> TYPE: DNA
<213> ORGANISM: Homo sapiens

<400> SEQUENCE: 14
ccaaccctca agagtcagat tcag                                           24

<210> SEQ ID NO 15
<211> LENGTH: 23
<212> TYPE: DNA
<213> ORGANISM: Homo sapiens

<400> SEQUENCE: 15
gcatctccca gaagaaggtg aag                                            23

<210> SEQ ID NO 16
<211> LENGTH: 23
<212> TYPE: DNA
<213> ORGANISM: Homo sapiens

<400> SEQUENCE: 16
taagtcctgg tctggttggt agc                                            23

<210> SEQ ID NO 17
<211> LENGTH: 20
<212> TYPE: DNA
<213> ORGANISM: Homo sapiens

<400> SEQUENCE: 17
tccgaagcct tccagtgtgt                                                20

<210> SEQ ID NO 18
<211> LENGTH: 20
<212> TYPE: DNA
<213> ORGANISM: Homo sapiens

<400> SEQUENCE: 18
acagagagcc gccatcagtc                                                20
```

-continued

<210> SEQ ID NO 19
<211> LENGTH: 22
<212> TYPE: DNA
<213> ORGANISM: Homo sapiens

<400> SEQUENCE: 19
tggtttccat tgaaagtgct gc                                              22

<210> SEQ ID NO 20
<211> LENGTH: 23
<212> TYPE: DNA
<213> ORGANISM: Homo sapiens

<400> SEQUENCE: 20
ttcctgggct tgactgactg tta                                             23

<210> SEQ ID NO 21
<211> LENGTH: 21
<212> TYPE: DNA
<213> ORGANISM: Homo sapiens

<400> SEQUENCE: 21
ttcccaaccc agactatgag c                                               21

<210> SEQ ID NO 22
<211> LENGTH: 20
<212> TYPE: DNA
<213> ORGANISM: Homo sapiens

<400> SEQUENCE: 22
aaggagggaa ctgaacggag                                                 20

<210> SEQ ID NO 23
<211> LENGTH: 20
<212> TYPE: DNA
<213> ORGANISM: Homo sapiens

<400> SEQUENCE: 23
acagatcttc ctgccagagc                                                 20

<210> SEQ ID NO 24
<211> LENGTH: 21
<212> TYPE: DNA
<213> ORGANISM: Homo sapiens

<400> SEQUENCE: 24
cacccaccag attggaatgg c                                               21

<210> SEQ ID NO 25
<211> LENGTH: 22
<212> TYPE: DNA
<213> ORGANISM: Mus musculus

<400> SEQUENCE: 25
ctgaggatgt gctgtctggg aa                                              22

<210> SEQ ID NO 26
<211> LENGTH: 20
<212> TYPE: DNA
<213> ORGANISM: Mus musculus

<400> SEQUENCE: 26
cctttgcctc cacttcggtc                                                 20

```
<210> SEQ ID NO 27
<211> LENGTH: 21
<212> TYPE: DNA
<213> ORGANISM: Mus musculus

<400> SEQUENCE: 27
tggagccagt caagagcatc a                                              21

<210> SEQ ID NO 28
<211> LENGTH: 24
<212> TYPE: DNA
<213> ORGANISM: Mus musculus

<400> SEQUENCE: 28
ggtaggtgaa gacaaaggaa gacg                                           24

<210> SEQ ID NO 29
<211> LENGTH: 23
<212> TYPE: DNA
<213> ORGANISM: Mus musculus

<400> SEQUENCE: 29
tttgagtttg tgaagcagag gcg                                            23

<210> SEQ ID NO 30
<211> LENGTH: 24
<212> TYPE: DNA
<213> ORGANISM: Mus musculus

<400> SEQUENCE: 30
caagcgaaga aactgcctca aaca                                           24

<210> SEQ ID NO 31
<211> LENGTH: 19
<212> TYPE: RNA
<213> ORGANISM: Artificial
<220> FEATURE:
<223> OTHER INFORMATION: small inhibitory RNA

<400> SEQUENCE: 31
gaacaguuau cuccagaag                                                 19

<210> SEQ ID NO 32
<211> LENGTH: 19
<212> TYPE: RNA
<213> ORGANISM: Artificial
<220> FEATURE:
<223> OTHER INFORMATION: small inhibitory RNA

<400> SEQUENCE: 32
gggauagccu cucuuacua                                                 19

<210> SEQ ID NO 33
<211> LENGTH: 19
<212> TYPE: RNA
<213> ORGANISM: Artificial
<220> FEATURE:
<223> OTHER INFORMATION: small inhibitory RNA

<400> SEQUENCE: 33
ggagacagac caacuagaa                                                 19

<210> SEQ ID NO 34
<211> LENGTH: 19
<212> TYPE: RNA
<213> ORGANISM: Artificial
```

```
<220> FEATURE:
<223> OTHER INFORMATION: small inhibitory RNA

<400> SEQUENCE: 34
agaccgagcc cuugauga                                              19

<210> SEQ ID NO 35
<211> LENGTH: 17
<212> TYPE: DNA
<213> ORGANISM: Artificial
<220> FEATURE:
<223> OTHER INFORMATION: oligodeoxynucleotide

<400> SEQUENCE: 35
tggtccagcg ccctgaa                                               17

<210> SEQ ID NO 36
<211> LENGTH: 17
<212> TYPE: DNA
<213> ORGANISM: Artificial
<220> FEATURE:
<223> OTHER INFORMATION: oligonucleotide

<400> SEQUENCE: 36
gaggttcctg ggggaca                                               17

<210> SEQ ID NO 37
<211> LENGTH: 17
<212> TYPE: DNA
<213> ORGANISM: Artificial
<220> FEATURE:
<223> OTHER INFORMATION: oligonucleotide

<400> SEQUENCE: 37
taagttgtcc cccatcc                                               17

<210> SEQ ID NO 38
<211> LENGTH: 17
<212> TYPE: DNA
<213> ORGANISM: Artificial
<220> FEATURE:
<223> OTHER INFORMATION: oligonucleotide

<400> SEQUENCE: 38
tatgaggaca tctcccg                                               17

<210> SEQ ID NO 39
<211> LENGTH: 17
<212> TYPE: DNA
<213> ORGANISM: Artificial
<220> FEATURE:
<223> OTHER INFORMATION: oligonucleotide

<400> SEQUENCE: 39
ggatgtgaaa ggctggc                                               17

<210> SEQ ID NO 40
<211> LENGTH: 17
<212> TYPE: DNA
<213> ORGANISM: Artificial
<220> FEATURE:
<223> OTHER INFORMATION: oligonucleotide

<400> SEQUENCE: 40
tggaaagtga atttgaa                                               17
```

```
<210> SEQ ID NO 41
<211> LENGTH: 17
<212> TYPE: DNA
<213> ORGANISM: Artificial
<220> FEATURE:
<223> OTHER INFORMATION: oligonucleotide

<400> SEQUENCE: 41
cttgacatac ctaccag                                                  17

<210> SEQ ID NO 42
<211> LENGTH: 17
<212> TYPE: DNA
<213> ORGANISM: Artificial
<220> FEATURE:
<223> OTHER INFORMATION: oligonucleotide

<400> SEQUENCE: 42
taacagccag gagtgct                                                  17

<210> SEQ ID NO 43
<211> LENGTH: 17
<212> TYPE: DNA
<213> ORGANISM: Artificial
<220> FEATURE:
<223> OTHER INFORMATION: oligonucleotide

<400> SEQUENCE: 43
ctaaactttt tataaaa                                                  17

<210> SEQ ID NO 44
<211> LENGTH: 17
<212> TYPE: DNA
<213> ORGANISM: Artificial
<220> FEATURE:
<223> OTHER INFORMATION: oligonucleotide

<400> SEQUENCE: 44
gagtccctgg tgctgcc                                                  17

<210> SEQ ID NO 45
<211> LENGTH: 17
<212> TYPE: DNA
<213> ORGANISM: Artificial
<220> FEATURE:
<223> OTHER INFORMATION: oligonucleotide

<400> SEQUENCE: 45
tagaaatgtt ctttgtg                                                  17
```

METHOD FOR ASSESSING ATHEROSCLEROSIS BY MEASURING EXPRESSION OF FOS OR DUSP1 IN MONOCYTES

CROSS REFERENCE TO RELATED APPLICATIONS

This application is the U.S. National Stage of International Application No. PCT/US2005/031469, filed Sep. 2, 2005, which was published in English under PCT Article 21(2), which in turn claims the benefit of U.S. Provisional Application No. 60/607,031, filed Sep. 3, 2004 and U.S. Provisional Application No. 60/618,275, filed Oct. 12, 2004, which are incorporated by reference herein in their entirety.

FIELD

This relates to the field of vascular disease such as atherosclerosis, more specifically to methods for detecting atherosclerosis using markers expressed in peripheral blood or secreted into the serum.

BACKGROUND

Cardiovascular disease is a major health risk throughout the industrialized world. Atherosclerosis, the most prevalent of cardiovascular diseases, is the principal cause of heart attack, stroke and gangrene of the extremities. It is also the principal cause of death in the United States.

Atherosclerosis is a complex disease involving many cell types and molecular factors (for review, see Ross, *Nature* 362:801-809, 1993). The process is believed to occur as a response to insults to the endothelial cell layer that lines the wall of the artery. The process includes the formation of fibrofatty and fibrous lesions or plaques, preceded and accompanied by inflammation. The advanced lesions of atherosclerosis may occlude an artery, and result from an excessive inflammatory-fibroproliferative response to numerous different forms of insult. For example, shear stresses are thought to be responsible for the frequent occurrence of atherosclerotic plaques in regions of the circulatory system where turbulent blood flow occurs, such as branch points and irregular structures.

The first event that is observed in the formation of an atherosclerotic plaque occurs when blood-borne monocytes adhere to the vascular endothelial layer and transmigrate through to the sub-endothelial space. Adjacent endothelial cells at the same time produce oxidized low density lipoprotein (LDL). These oxidized LDLs are then taken up in large amounts by the monocytes through scavenger receptors expressed on their surfaces. The lipid-filled monocytes are termed "foam cells," and are the major constituent of the fatty streak. Interactions between foam cells and the endothelial and SMCs which surround them can eventually lead to smooth muscle cell proliferation and migration, and the formation of a fibrous plaque. Such plaques occlude the blood vessel concerned and restrict the flow of blood, resulting in ischemia.

Ischemia is characterized by a lack of oxygen supply in tissues of organs due to inadequate perfusion. The most common cause of ischemia in the heart is atherosclerotic disease of epicardial coronary arteries. By reducing the lumen of these vessels, atherosclerosis causes an absolute decrease in myocardial perfusion in the basal state or limits appropriate increases in perfusion when the demand for flow is augmented.

The principal surgical approaches to the treatment of ischemic atherosclerosis are bypass grafting, endarterectomy and percutaneous transluminal angioplasty (PCTA). The latter approach often fails due to restenosis, in which the occlusions recur and often become even worse. This is estimated to occur at an extraordinarily high (30-50%) rate. It appears that much of the restenosis is due to further inflammation, smooth muscle accumulation and thrombosis. There remains a need for methods to diagnose and/or treat atherosclerosis. Most current methods involve evaluation of the arteries themselves or vascular function.

SUMMARY

It is disclosed herein that FOS and DUSP1 expression is increased in mononuclear cells, such as in peripheral blood monocytes, in subjects with atherosclerosis. It is also disclosed that following an effective treatment for atherosclerosis, FOS and DUSP1 is decreased in peripheral blood monocytes, serum and/or plasma.

In one embodiment, a non-invasive method for the diagnosis of atherosclerosis, or for determining the risk for the development or progression of atherosclerosis, is provided. In one example, the method includes assaying the expression of FOS, DUSP1, or both FOS and DUSP1 in monocytes from the subject, wherein an increase in the expression of FOS, DUSP1, or both FOS and DUSP1 in monocytes in the sample as compared to a control indicates that the subject has atherosclerosis. In one example, the monocytes are in a peripheral blood sample. In another example, FOS and or DUSP1 are assessed in a serum or plasma sample from the subject.

In another embodiment, a method is disclosed for determining if a pharmaceutical agent is effective for treatment of atherosclerosis in a subject. The method includes assaying the expression of FOS, DUSP1, or both FOS and DUSP1 in a monocytes treated with the pharmaceutical agent, wherein a decrease in the expression of FOS, DUSP1, or both FOS and DUSP1 in monocytes in the sample as compared to a control indicates that the pharmaceutical agent is effective for the treatment of atherosclerosis. In one example, a peripheral blood sample is utilized that includes monocytes. In another example, a monocyte cell line is utilized.

The foregoing and other features and advantages will become more apparent from the following detailed description of several embodiments, which proceeds with reference to the accompanying figures.

BRIEF DESCRIPTION OF THE FIGURES

FIG. 1A shows normalized fold-change expression levels of the candidate genes are color-coded (red, induced; green, repressed). The subjects are ordered by the average expression values of the six genes (AVG). The three groups are composed of: A, younger controls A1 and A2; Controls, normal subjects C1-C19; and Patients, carotid endarterectomy patients P1-P25. FIG. 1B is a bar graph showing relative expression levels of the top two candidate genes, FOS and DUSP1, and plasma hsCRP levels in Control (n=19) versus Patient (n=25). Values shown as mean±SE. P values for difference between control and patient were calculated using Student's t-test. FIG. 1C is a bar graph of controls and patients ordered by the relative level of FOS expression within each group. Diamonds indicate history of coronary revascularization either by angioplasty or coronary artery bypass graft surgery (Revasc.); squares, current HMG CoA reductase inhibitor treatment (Statin); circles, current aspirin treatment (ASA). All RT-PCR measurements done in duplicates and repeated at least two times. FIG. 1D is a line graph of receiver operating characteristic curves for the utility of FOS (solid circle and line) and hsCRP (square and dashed line) at identifying coronary revascularization patients. FIG. 1E is a bar graph of controls and patients ordered by the relative level of DUSP1 expression within each group. The patient (P) and control (C) numbers correspond to the numbering in FIG. 1C, thus the clinical information denoted by Diamonds, Squares and Circles for (Revasc.), (Statin) and (ASA), is maintained in this panel. There is a high correlation between FOS and DUSP1 expression levels between controls and patients.

FIG. 2A is a digital image of fresh frozen sections of human carotid artery plaques stained with hematoxylin and eosin (H&E), negative control immunoglobulin (Control Ig) and antibodies against CD14 or FOS. CD14+ staining of macrophages colocalizes with FOS immunoreactivity (25× magnification). Note that the CD14 staining gives a more diffuse appearance consistent with cell surface plasma membrane staining while the FOS pattern is more punctate consistent with nuclear localization. For the digital image shown as FIG. 2B, from four patients, the corresponding mononuclear cell (MNC), circulating monocyte (Mono) and carotid plaque purified macrophage (Mac) preparations were used for quantitative RT-PCR. The normalized expression levels shown were obtained as described in FIG. 1A. Note the progressively higher pattern of candidate gene expression associated with increasing concentration of monocytes and activation into macrophages. FIG. 2C is a digital image wherein five different human monocytic cell lines were stimulated with 20 nM PMA for the indicated times (h) and RT-PCR performed as described above. FIG. 2D is a bar graph showing the difference in relative expression of FOS mRNA in splenocytes from ApoE gene knockout (KO, n=11) and wild-type (WT, n=14) mice. Values expressed as mean±SE, P=0.04.

FIG. 3A is a bar graph and a digital image wherein THP1 cells were pretreated with simvastatin and/or mevalonate for 20 hours prior to stimulation with 2 nM PMA. Cell adhesion was determined 4 hours after PMA stimulation; cumulative MCP-1 release into medium was assayed 24 hours after PMA stimulation. Western blot shows FOS protein levels after 4 hours of PMA stimulation for the indicated conditions. P values for the difference in cell adhesion and MCP-1 release after statin treatment were 0.004 and 0.04, respectively. FIG. 3B is a bar graph and a digital image wherein THP1 cells were stimulated with 2 nM PMA 30 minutes after siRNA transfection for 4 hours. Control (−) cells were mock transfected without siRNA as a transfection control. The difference between the nonspecific sequence (NS) and FOS target sequence (FOS) siRNAs were significant, P=0.006. Data shown are representative of experiments repeated at least three times in duplicates or triplicates.

FIG. 5A is a set of plots from flow cytometry showing the relative distribution profiles of CD14− (negative) and CD14+ (positive with anti-CD14 antibody conjugated to fluorescein isothiocyanate (FITC)) cells in the mononuclear cell (MNC), purified monocyte (Mono) and monocyte-depleted (Non-mono) fractions. FIG. 5B is a set of digital images of RT-PCR of undiluted (1) and one-tenth diluted (0.1) cDNA from different fractions of blood and carotid plaque purification. Cell markers: control genes, glyceraldehyde-3-phosphate dehydrogenase (GAPD), and translation initiation factor (TIF); monocyte, CD14; macrophage, macrophage mannose receptor (CD206); lymphocyte, CD3; platelet, glycoprotein IIb (GPIIb). NTC, no template control; RT−, no reverse transcriptase; SN, plaque suspension cells after CD14+ macrophage depletion.

SEQUENCE LISTING

Figure 1A:
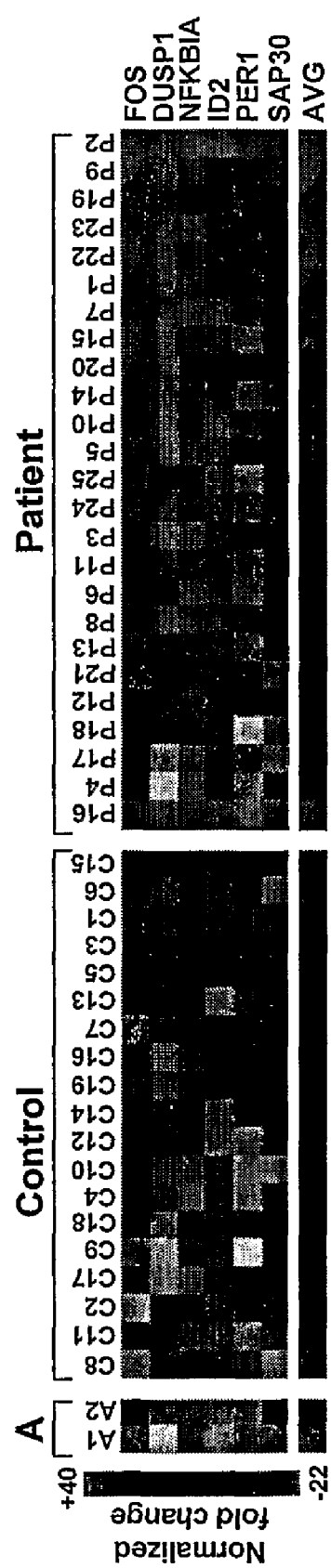
FIGS. 1A-1E are digital images and graphs showing mononuclear cell mRNA expression levels of the candidate genes identified by SAGE in normal control subjects and carotid endarterectomy patients.

The nucleic and amino acid sequences listed in the accompanying sequence listing are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand. In the accompanying sequence listing:

SEQ ID NOs: 1-2 are the nucleic acid sequence of a human GAPD forward and a reverse primer, respectively.

SEQ ID NOs: 3-4 are the nucleic acid sequence of a human TIF forward and a reverse primer, respectively.

SEQ ID NOs: 5-6 are the nucleic acid sequence of a human FOS forward and a reverse primer, respectively.

SEQ ID NOs: 7-8 are the nucleic acid sequence of a human DUSP1 forward and a reverse primer, respectively.

SEQ ID NOs: 9-10 are the nucleic acid sequence of a human NFKB1A forward and a reverse primer, respectively.

SEQ ID NOs: 11-12 are the nucleic acid sequence of a human ID2 forward and a reverse primer, respectively.

SEQ ID NOs: 13-14 are the nucleic acid sequence of a human PER1 forward and a reverse primer, respectively.

SEQ ID NOs: 15-16 are the nucleic acid sequence of a human SAP30 forward and a reverse primer, respectively.

SEQ ID NOs: 17-18 are the nucleic acid sequence of a human CD14 forward and a reverse primer, respectively.

SEQ ID NOs: 19-20 are the nucleic acid sequence of a human CD206 forward and a reverse primer, respectively.

SEQ ID NOs: 21-22 are the nucleic acid sequence of a human CD3 forward and a reverse primer, respectively.

SEQ ID NOs: 23-34 are the nucleic acid sequence of a human GP11b forward and a reverse primer, respectively.

SEQ ID NOs: 25-26 are the nucleic acid sequence of a mouse TIF forward and a reverse primer, respectively.

SEQ ID NOs: 27-28 are the nucleic acid sequence of a mouse FOS forward and a reverse primer, respectively.

SEQ ID NOs: 29-30 are the nucleic acid sequence of a mouse DUSP1 forward and a reverse primer, respectively.

SEQ ID NOs: 31-34 are FOS siRNA target nucleic acid sequences.

SEQ ID NO: 35 is the nucleic acid sequence of the CD14 SAGE tag sequence.

SEQ ID NO: 36 is the nucleic acid sequence of the CD163 SAGE tag sequence.

SEQ ID NO: 37 is the nucleic acid sequence of the CD3E SAGE tag sequence.

SEQ ID NO: 38 is the nucleic acid sequence of the CD79A SAGE tag sequence.

SEQ ID NO: 39 is the nucleic acid sequence of the CD99 SAGE tag sequence.

SEQ ID NO: 40 is the nucleic acid sequence of the FOS SAGE tag sequence.

SEQ ID NO: 41 is the nucleic acid sequence of the dual specificity phosphatase 1 (DUSP1) tag sequence.

SEQ ID NO: 42 is the nucleic acid sequence of the NF kappa gene in B-cell inhibitor (NFKB1A) SAGE tag sequence.

SEQ ID NO: 43 is the nucleic acid sequence of the inhibitor of DNA 2 (ID2) SAGE tag sequence.

SEQ ID NO: 44 is the nucleic acid sequence of the period homolog 1 (PER1) SAGE tag sequence.

SEQ ID NO: 45 is the nucleic acid sequence of the sin 3-associated polypeptide, 30 kDa (SAP30) SAGE tag sequence.

DETAILED DESCRIPTION

I. Abbreviations

| | |
|---|---|
| AVG: | average |
| BMI: | body mass index |
| CEA: | Carotid endarterectomy |
| DUSP1: | dual specificity phosphatase 1 |
| FITC: | fluorescein isothiocyanate |
| FOS: | Biskis-Jinkins osteosarcoma |
| GADP: | glyceraldehyde-3-phosphate dehydrogenase |
| GPIIb: | glycoprotein IIb |
| hsCRP: | high sensitivity C-reactive protein |
| ID1: | inhibitor of DNA binding 2 |
| kDa: | kilodaltons |
| KO: | knock-out |
| MAPK: | mitogen activated protein kinase |
| MCP-1: | monocyte chemoattractant protein 1 |
| MNC: | mononuclear cells |
| NTC: | no template control |
| PCR: | polymerase chain reaction |
| PER1: | period homolog 1 |
| PMA: | phorbo 12-myristate 13-acetate |
| ROC: | receive operating characteristic |
| RT: | reverse transcriptase |
| SAP30: | sin-3 associated polypeptide, 30 kDa |
| SAGE: | serial analysis of gene expression |
| SE: | standard error |
| siRNA: | small inhibitory RNA |
| SN: | plaque suspension cells after CD14+ macrophage depletion |
| TIF: | translation initiation factor |
| WT: | wild-type |

II. Terms

Unless otherwise noted, technical terms are used according to conventional usage. Definitions of common terms in molecular biology may be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

In order to facilitate review of the various embodiments of this disclosure, the following explanations of specific terms are provided:

Alter: A change in an effective amount of a substance of interest, such as a polynucleotide or polypeptide. The amount of the substance can changed by a difference in the amount of the substance produced, by a difference in the amount of the substance that has a desired function, or by a difference in the activation of the substance. The change can be an increase or a decrease. The alteration can be in vivo or in vitro.

In several embodiments, altering an amount of a polypeptide or polynucleotide is at least about a 50%, 60%, 70%, 80%, 90%, 95%, 96%, 97%, 98%, 99%, or 100% increase or decrease in the effective amount (level) of a substance. In specific example, an increase of a polypeptide or polynucleotide is at least about a 50%, 60%, 70%, 80%, 90%, 95%, 96%, 97%, 98%, 99%, or 100% increase in FOS and/or DUSP1 polypeptide or polynucleotide as compared to a control, a statistical normal, or a standard value chosen for specific study. In another specific example, a decrease of a polypeptide or polynucleotide, such as following the initiation of a therapeutic protocol, is at least about a 50%, 60%, 70%, 80%, 90%, 95%, 96%, 97%, 98%, 99%, or 100% decrease in FOS and/or DUSP1 polypeptide or polynucleotide as compared to a control, a statistical normal, or a standard value chosen for specific study.

Atherosclerosis: The progressive narrowing and hardening of a blood vessel over time. Atherosclerosis is a common form of ateriosclerosis in which deposits of yellowish plaques (atheromas) containing cholesterol, lipoid material and lipophages are formed within the intima and inner media of large and medium-sized arteries. Treatment of atherosclerosis includes reversing or slowing the progression of atherosclerosis, for example as measured by the presence of atherosclerotic lesions and/or functional signs of the disease, such as improvement in cardiovascular function as measured by signs (such as peripheral capillary refill), symptoms (such as chest pain and intermittent claudication), or laboratory evidence (such as that obtained by EKG, angiography, or other imaging techniques). "Assessing atherosclerosis" indicates determining if a subject of interest has atherosclerosis, determining the prognosis of the subject of interest, and/or determining if a therapeutic regimen administered to the subject is effective in treating the subject.

Binding or stable binding: An association between two substances or molecules, such as the hybridization of one nucleic acid molecule to another (or itself), the association of an antibody with a peptide, or the association of a protein with another protein or nucleic acid molecule. An oligonucleotide molecule binds or stably binds to a target nucleic acid molecule if a sufficient amount of the oligonucleotide molecule forms base pairs or is hybridized to its target nucleic acid molecule, to permit detection of that binding.

Binding can be detected by any procedure known to one skilled in the art, such as by physical or functional properties of the formed complexes, such as a target:oligonucleotide complex or a target:antibody complex. For example, binding can be detected functionally by determining whether binding has an observable effect upon a biosynthetic process such as expression of a gene, DNA replication, transcription, translation, and the like.

Physical methods of detecting the binding of complementary strands of nucleic acid molecules, include but are not limited to, such methods as DNase I or chemical footprinting, gel shift and affinity cleavage assays, Northern blotting, dot blotting and light absorption detection procedures. For example, one method involves observing a change in light absorption of a solution containing an oligonucleotide (or an analog) and a target nucleic acid at 220 to 300 nm as the temperature is slowly increased. If the oligonucleotide or analog has bound to its target, there is a sudden increase in absorption at a characteristic temperature as the oligonucleotide (or analog) and target disassociate from each other, or melt. In another example, the method involves detecting a signal, such as a detectable label, present on one or both nucleic acid molecules (or antibody or protein as appropriate).

In one example, the binding between an oligomer and its target nucleic acid is characterized by the temperature ($T_m$) at which 50% of the oligomer is melted from its target. A higher ($T_m$) means a stronger or more stable complex relative to a complex with a lower ($T_m$).

Blood vessel: The vessels through which blood circulates. In general, blood vessels are elastic tubular channels that are lined with endothelium. Blood vessels include the arteries, veins and capillaries. Specific, non-limiting examples of a blood vessel include a vena cava, a thoracic aorta, a saphanous vein, a mammary artery, the brachial artery and a capillary. In another embodiment, a blood vessel includes the smaller arteries and veins. In yet another embodiment, a blood vessel is a capillary of the microvascular circulation.

Buffy coat: A thin yellow or white layer of leukocytes that appears on top of a mass of packed red cells when whole blood is centrifuged.

Cardiovascular: Pertaining to the heart and/or blood vessels.

Cardiovascular risk: The likelihood of the development of disorders related to the cardiovascular system, such as, but not limited to, myocardial ischemia and infarction, intermittent claudication, bowel ischemia, retinal ischemia, transient ischemic attacks, ischemic strokes, and other conditions associated with cardiovascular dysfunction. In a specific non-limiting example, the disorder is myocardial ischemia or infarction.

Cholesterol lowering agent: An agent, such as a pharmaceutical, vitamin, or small molecule, that lowers the level of cholesterol in a subject. One of skill in the art can readily identify assays, such as blood screening, to determine the effect of cholesterol. Agents include, but are not limited to, niacin, the statins (e.g., Zocor™, Lipitor™, Pravacol™, Lescor™, Mevacor™), binding resins (e.g., Questran™), and fibrates (e.g. Lopid™, Lipidil Micro™).

DUSP1: Dual specificity phosphatase 1, which is known to be induced by oxidative stress and heat shock. DUSP1 has also been called CL100, MVH1, MKP-1 and DTPN10. Exemplary human DUSP1 amino acid and nucleic acid sequence can be found at GenBank Accession No. U01669 (Jun. 11, 1994) and X68277 (Apr. 18, 2005), and Swiss-Prot No. P28562 (Feb. 23, 2996), which are incorporated herein by reference. In humans, the DUSP1 gene is encoded on chromosome 5. DUSP1 is a dual specification phosphatase that dephosphorylates MAP kinase ERK at Tyr-185. Orthogs from chimpanzee, rat, mouse, and zebrafish have been identified (see GeneCard for DUSP1, GC05M1721127, which is available on the internet at the Weizmann Institute of Science Website).

FOS: An oncogene, Finkel-Biskis-Jinkins osteosarcoma (FOS) gene. FOS was identified in a mouse osteosarcoma, encoding a transcription factor. The product of this oncogene works with the product of another oncogene, the jun oncogene, to abnormally change the rate of transcription of certain other genes. c-FOS is the cellular homolog of the viral v-FOS oncogene found in FBJ (Finkel-Biskis-Jinkins) and FBR murine osteosarcoma viruses (MSV). The human FOS gene maps to chromosome 14q21-q31. FOS has been identified as TIS28, a gene inducible in several cell types by Phorbol esters. Exemplary amino acid and nucleic acid sequence for the murine and human FOS are shown in GenBank Accession No. BC029814 (Jun. 30, 2004) and V 01512 (Nov. 21, 2004), respectively, and is shown as Swiss-Prot No. P0110 (Jul. 1, 1986), which are incorporated herein by reference.

Without being bound by theory, c-FOS is thought to have an important role in signal transduction, cell proliferation and differentiation. It is a nuclear protein which, in combination with other transcription factors (for example: c-jun) acts as a trans-activating regulator of gene expression. Orthogs from chimpanzee, rat, mouse, and zebrafish have been identified (see GeneCard for FOS, GC14P074815, which is available on the internet at the Weizmann Institute of Science website).

Framingham Risk Score: A risk factor score that is used for predicting future risk of coronary artery disease in individuals free of disease, based on the measurement of risk factors including age, gender, systolic blood pressure, cigarette smoking, glucose intolerance, left ventricular hypertrophy, as well as total cholesterol, low density lipoprotein (LDL) and high density lipoprotein (HDL) levels (Wilson et al., *Am J Cardiol* 59:91G-94G, 1987).

Leukocyte: Cells in the blood, also termed "white cells," that are involved in defending the body against infective organisms and foreign substances. Leukocytes are produced in the bone marrow. There are five main types of white blood cells, subdivided between two main groups: polymorphonuclear leukocytes (neutrophils, eosinophils, basophils) and mononuclear leukocytes (monocytes and lymphocytes). When an infection is present, the production of leukocytes increases.

Lymphocytes: A type of white blood cell that is involved in the immune defenses of the body. There are two main types of lymphocytes: B cell and T cells.

Microarray: An "array" is an arrangement of molecules, such as biological macromolecules (such as peptides or nucleic acid molecules) or biological samples (such as tissue sections), in addressable locations on or in a substrate. A "microarray" is an array that is miniaturized so as to require or be aided by microscopic examination for evaluation or analysis. Arrays including biological materials are sometimes called DNA chips or biochips. Generally, DNA is either spotted, using pins or an ink-jet printer, or synthesized directly on the array using PCR or photolithography. The DNA may be either double-stranded copies of transcripts or shorter single-stranded oligonucleotides. In one embodiment, for microarray analysis, RNA is first extracted from a sample; the RNA can be amplified prior to analysis. Subsequently, the RNA itself, complementary DNA, or amplified RNA is labeled. The labeled nucleic acid is hybridized, competitively or non-competitively, to the microarray. Complementary sequences remain bound to the array and unbound sequences are washed off. Expressed genes are identified by the position of bound probes on the array. Microarrays are available from a number of commercial sources, or can be produced in individual laboratories. In addition, computer software that can be used to analyze the microarray data is available commercially from a number of sources and on the internet (see the dchip website, or the tigr website, for examples).

Hybridization: To form base pairs between complementary regions of two strands of DNA, RNA, or between DNA and RNA, thereby forming a duplex molecule. Hybridization conditions resulting in particular degrees of stringency will vary depending upon the nature of the hybridization method and the composition and length of the hybridizing nucleic acid sequences. Generally, the temperature of hybridization and the ionic strength (such as the Na+ concentration) of the hybridization buffer will determine the stringency of hybridization. Calculations regarding hybridization conditions for attaining particular degrees of stringency are discussed in Sambrook et al., (1989) Molecular Cloning, second edition, Cold Spring Harbor Laboratory, Plainview, N.Y. (chapters 9 and 11). An exemplary non-limiting set of very high stringency conditions (detects sequences that share 90% identity) include hybridization in 5×SSC at 65° C. for 16 hours, washing twice in 2×SSC at room temperature (RT) for 15 minutes each, and washing twice in 0.5×SSC at 65° C. for 20 minutes each. An exemplary non-limiting set of high stringency conditions (detects sequences that share 80% identity or greater) include hybridization in 5×-6×SSC at 65° C.-70° C. for 16-20 hours, washing twice in 2×SSC at RT for 5-20 minutes each, and washing twice in 1×SSC at 55° C.-70° C. for 30 minutes each.

Label: An agent capable of detection, for example by ELISA, spectrophotometry, flow cytometry, or microscopy. For example, a label can be attached to a nucleic acid molecule or protein, thereby permitting detection of the nucleic acid molecule or protein. Examples of labels include, but are not limited to, radioactive isotopes, enzyme substrates, cofactors, ligands, chemiluminescent agents, fluorophores, haptens, enzymes, and combinations thereof. Methods for labeling and guidance in the choice of labels appropriate for various purposes are discussed for example in Sambrook et al. (Molecular Cloning: A Laboratory Manual, Cold Spring Harbor, N.Y., 1989) and Ausubel et al. (In Current Protocols in Molecular Biology, John Wiley & Sons, New York, 1998).

Monocyte: A relatively large mononuclear leukocyte (16-22 μm in diameter). Monocytes normally constitute 3-7% of the leukocytes of the circulating blood, and are normally found in lymph nodes, spleen, bone marrow and loose connective tissue. When treated with histological dyes, monocytes manifest an abundant pale blue or blue-gray cytoplasm that contains numerous, fine, dust-like, red-blue granules; vacuoles are frequently present; the nucleus is usually indented, or slightly folded, and has a stringy chromatin structure that seems more condensed where the delicate strands are in contact. Generally, monocytes have an ovoid or kidney-shaped nucleus, containing lacy, linear chromatin, and abundant gray-blue cytoplasm filled with fine reddish and azurophilic granules. Circulating monocytes in blood differentiate into macrophages when they migrate into tissues.

Polynucleotide: A linear nucleotide sequence, including sequences of greater than 100 nucleotide bases in length.

Polypeptide: Any chain of amino acids, regardless of length or post-translational modification (e.g., glycosylation or phosphorylation).

Purified or Isolated: The term "purified" or "isolated" does not require absolute purity; rather, it is intended as a relative term. A purified nucleic acid or protein is isolated or purified away from other biological components in the cell of the organism in which the component naturally occurs, i.e., other chromosomal and extrachromosomal DNA and RNA, and proteins Nucleic acids, peptides and proteins which have been "isolated" thus include nucleic acids and proteins purified by standard purification methods. The term also embraces nucleic acids, peptides and proteins prepared by recombinant expression in a host cell as well as chemically synthesized nucleic acids.

Thus, for example, a purified cell preparation is one in which the cell, protein or nucleic acid referred to is more pure than the cell in its natural environment within a tissue. In one embodiment, a "substantially purified" population of a specific cell type is a composition of cells that includes less than about 20%, less than about 15%, or less than about 10% of cells of a different phenotype. Thus, a substantially purified population of cells includes greater than 80%, greater than 85%, or greater than 90% of the cells of interest. In another embodiment, a process that produces a purified population of cells is a process that produces a population of cells so that more than 50% of the resulting population is the cell type of interest.

Statin: Any of a class of lipid-lowering drugs that reduce serum cholesterol levels by inhibiting a key enzyme involved in the biosynthesis of cholesterol. Example statins include atorvastatin (Lipitor®), fluvastatin (Lescol®), lovastatin (Mevacor®, Altocor®, not marketed in the UK), pravastatin (Pravachol®, Selektine®, Lipostat®), rosuvastatin (Crestor®), simvastatin (Zocor®). There are two groups of statins: (1) Fermentation-derived: lovastatin, simvastatin and pravastatin, and (2) Synthetic statins: fluvastatin, atorvastatin, cerivastatin and rosuvastatin. Generally, statins act by competitively inhibiting 3-hydroxy-3-methylglutaryl coenzyme A (HMG CoA) reductase, an enzyme of the HMG-CoA reductase pathway, the body's metabolic pathway for the synthesis of cholesterol.

The structure of one exemplary statin, Lovastatin, is shown below.

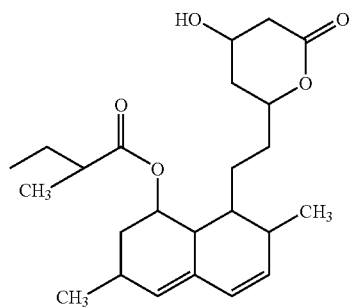

Subject: Any subject that has a vascular system and has hematopoietic cells. In one embodiment, the subject is a non-human mammalian subject, such as a monkey, mouse, rat, rabbit, pig, goat, sheep or cow. In another embodiment, the subject is a human subject.

Therapeutically effective amount: An amount of a pharmaceutical preparation that alone, or together with a pharmaceutically acceptable carrier or one or more additional therapeutic agents, induces the desired response. A therapeutic agent, such as an anticoagulant, is administered in therapeutically effective amounts.

Effective amounts a therapeutic agent can be determined in many different ways, such as assaying for a reduction in atherosclerotic disease or improvement of physiological condition of a subject having vascular disease. Effective amounts also can be determined through various in vitro, in vivo or in situ assays.

Therapeutic agents can be administered in a single dose, or in several doses, for example daily, during a course of treatment. However, the effective amount of can be dependent on the source applied, the subject being treated, the severity and type of the condition being treated, and the manner of administration.

In one example, it is an amount sufficient to partially or completely alleviate symptoms of vascular disease within a subject. Treatment can involve only slowing the progression of the vascular disease temporarily, but can also include halting or reversing the progression of the vascular disease permanently. For example, a pharmaceutical preparation can decrease one or more symptoms of vascular disease, for example decrease a symptom by at least 20%, at least 50%, at least 70%, at least 90%, at least 98%, or even at least 100%, as compared to an amount in the absence of the pharmaceutical preparation.

Treating a disease: "Treatment" refers to a therapeutic intervention that ameliorates a sign or symptom of a disease or pathological condition, such a sign, parameter or symptom of vascular disease (for example, atherosclerosis). Treatment can also induce remission or cure of a condition, such as vascular disease. In particular examples, treatment includes preventing a disease, for example by inhibiting the full development of a disease, such as preventing development of vascular disease. Prevention of a disease does not require a total absence of vascular disease. For example, a decrease of at least 50% can be sufficient.

Vascular function: The function of the blood vessels. Decreased vascular function is associated with atherosclerosis, myocardial infarction, intermittent claudication, bowel ischemia, retinal ischemia, transient ischemic attacks (TIAs), ischemic strokes, restenosis after angioplasty, transplant atherosclerosis, unstable angina, sudden death and alterations in blood pressure.

Vascular function assessment: An assay that measures the function of the vascular system. Assays include measurement of a parameter of the blood, assays of arterial hyperplasia, vascular contractility measurements, brachial reactivity measurements, and morphometric measurements. Similarly, an endothelial cell assessment is a test that measures a function or parameter of an endothelial cell. "Decreased vascular function" indicates a decrease in any function of the blood vessels, as compared to a standard value or a control sample. Thus, in one example, decreased vascular function is a decrease in a vascular contractility, as compared to a known value for normal vascular contractility. In another example, decreased vascular function is the lower contractility of a blood vessel as compared to the contractility of a vessel known to not be affected by a disease or a disorder. In a further example, decreased vascular function is a lower vascular contractility as compared to the contractility of a vessel from the same subject at an earlier time point. "Cardiovascular risk" is the probability that a subject has or will develop a vascular disease in the future.

Vascular tissue: Tissue consisting of, or containing, vessels as an essential part of a structure. Vascular tissue operates by means of, or is made up of an arrangement of, vessels. Vascular tissue includes the arteries, veins, capillaries, lacteals, microvasculature, etc. In one embodiment, vascular tissue includes a highly vascularized organ (e.g. the lung). In another embodiment, vascular tissue is a blood vessel, or a portion thereof. Cells isolated from a vascular tissue are a population of cells isolated from the remaining components of the tissue.

Assessment of Vascular Function

A method of assessing vascular function in a subject is disclosed herein. Specifically, the method is of use in assessing (for example, determining the diagnosis or prognosis of) atherosclerosis. In several embodiments, the method includes assaying expression of FOS mRNA or the presence of FOS polypeptide. In additional embodiments, the method includes assaying expression of DUSP1 mRNA or the presence of DUSP1 polypeptide. The method can include monitoring FOS and/or DUSP1 in blood, serum or plasma.

The method can be used, for example, to predict future cardiovascular risk. Specifically, the method can be used to predict risk for myocardial infarction, intermittent claudication, bowel ischemia, retinal ischemia, transient ischemic attacks (TIAs), ischemic strokes, restenosis after angioplasty, transplant atherosclerosis, unstable angina, sudden death, and other conditions associated with cardiovascular dysfunction. In one specific, non-limiting example, the assessment of FOS or DUSP1 is of use in predicting cardiovascular risk for myocardial ischemia and/or infarction. Cardiovascular risk indicates the potential for a future cardiovascular event, such as myocardial infarction, intermittent claudication, bowel ischemia, retinal ischemia, transient ischemic attacks (TIAs), ischemic strokes, restenosis after angioplasty, transplant atherosclerosis, unstable angina, sudden death, and other conditions associated with cardiovascular dysfunction. Factors involved in cardiovascular risk include, but are not limited to, serum cholesterol, hypertension, diabetes, sex and age. The method can also be used to assess the severity of a disease, such as atherosclerosis.

Methods are provided herein for evaluating vascular risk, for example for determining whether a subject, such as an otherwise healthy subject, or a subject suspected or at risk of having vascular disease, has vascular disease or will likely develop vascular disease in the future. In particular examples, the method can determine with a reasonable amount of sensitivity and specificity whether a subject has or will likely develop a vascular disease in the future. In some examples, isolated or purified PBMCs, serum, blood or plasma obtained from the subject are used to predict the subject's risk of vascular disease. In one example, the subject is apparently healthy, such as a subject who does not exhibit symptoms of vascular disease (for example has not previously had an acute adverse vascular event such as a myocardial infarction or a stroke). In some examples, a healthy subject is one that if examined by a medical professional, would be characterized as healthy and free of symptoms of vascular disease. In another example, the subject is suspected of having a vascular disease, or is suspected of being at risk of developing a vascular disease in the future. For example, such a subject may have elevated cholesterol or tri-glyceride levels, elevated C-reactive protein levels, or high blood pressure.

In a specific, non-limiting example, the expression of FOS and/or DUSP1 in monocytes is used to non-invasively diagnose atherosclerosis. For example, expression of FOS and/or DUSP1 can be used to assess the severity and/or the progression of the disease. In one embodiment, the expression of FOS and/or DUSP1 in monocytes is assessed. The monocytes can be in an atherosclerotic lesion or can be circulating monocytes in the peripheral blood. In additional embodiments, the amount of FOS into the plasma or serum is assessed. Thus, in several examples, the method includes measuring the expression of FOS and/or DUSP1 in the peripheral blood, plasma, serum, or in peripheral blood mononuclear cells, to determine the risk for developing a cardiovascular condition such as, but not limited to, atherosclerosis. Such assessments can assist in determining whether to initiate therapy, for example, with lifestyle (including dietary) intervention or pharmacologic (drug) therapy.

The methods disclosed herein include assaying the expression of FOS, DUSP1, or both FOS and DUSP1. An increase in the expression of FOS and/or DUSP1 in a sample including monocytes as compared to a control sample indicates decreased vascular function, for example, increased future cardiovascular risk or development of atherosclerosis. In one specific, non-limiting example, an assessment of the risk of a subject to develop vascular disease, or an assessment of vascular function is made by evaluating the expression of FOS and/or DUSP1 in peripheral blood mononuclear cells (PBMC).

In a further specific, non-limiting example the expression of FOS and/or DUSP1 are used to assess the efficacy of a therapeutic protocol. The treatment protocol can include any therapy for atherosclerosis designed to reverse or slow the progression of atherosclerosis, including but not limited to treatment with statins, niacin or other cholesterol-lowering agents, anti-inflammatory agents, or any other pharmaceutical compound. In this embodiment, a sample including monocytes, and/or a sample of blood, serum or plasma, can be taken from a subject prior to initiation of therapy. After therapy is initiated, an additional sample including monocytes, and/or a sample of blood, serum or plasma, is taken from the subject. A decrease in the amount of FOS and/or DUSP1 indicates that the therapy is efficacious. In addition, the subject can be monitored over time to evaluate the continued effectiveness of the therapeutic protocol. The effect of different dosages can also be evaluated, by comparing the expression of FOS and/or DUSP1 in a sample from the subject receiving a first dose to the expression of FOS and/or DUSP1 in a sample from the subject receiving a second (different) dose.

A variety of methods can be employed to detect FOS and/or DUSP1 expression in monocytes in an atherosclerotic lesion or in the peripheral blood, serum, or plasma. These methods include the use of nucleic acid probes, antibodies or other analytical techniques such as mass spectrometry to detect FOS and/or DUSP1 expression. The expression of FOS and/or DUSP1 is assessed in monocytes, such as monocytes in an atherosclerotic lesion or peripheral blood monocytes, or in a blood, peripheral blood, or serum sample. In one specific, non-limiting example, the method specifically excludes detection of FOS and/or DUSP1 in vascular smooth muscle, such that the expression of FOS and/or DUSP1 is evaluated in monocytes only (or in the blood, plasma or serum only). Thus, in one embodiment, the assay system is designed to distinguish expression of FOS and/or DUSP1 in monocytes. Thus, in one embodiment, the expression of FOS and/or DUSP1 is not evaluated in the vascular tissue, such as in vascular smooth muscle. In another embodiment, the assay is designed to detect the release into plasma from the expression of FOS and DUSP1 in vascular tissue. In several examples, the assay can be performed in isolated peripheral blood monocytes (PBMC), plasma, blood or serum.

Detection of FOS and DUSP1 Nucleic Acids

In one embodiment, nucleic acid based methods are utilized. These methods include serial analysis of gene expression (SAGE techniques), RT-PCR, quantitative PCR, real time PCR, Northern blot, dot blots, microarrays, amongst others. Generally, with regard to nucleic acids, any method can be utilized provided it can detect the expression of target gene mRNA (FOS and/or DUSP1) as compared to a control. One of skill in the art can readily identify an appropriate control, such as a sample from a subject known not to have a disorder (a negative control), a sample from a subject known to have a disorder (a positive control), or a known amount of nucleic acid encoding FOS and/or DUSP1 (a standard or a normal level found in a healthy subject). Statistically normal levels can be determined for example, from a subject with known not to have atherosclerosis, and to at low risk for a cardiac event. In one non-limiting example, normal levels can be assessed by measuring FOS and/or DUSP1 in the blood, serum, or plasma of young adults, who do not smoke or drink, exercise regularly, have no known history of cardiac events, and no familial history of heart disease.

The methods described herein may be performed, for example, by utilizing pre-packaged diagnostic kits comprising at least one specific nucleic acid probe, which may be conveniently used, such as in clinical settings, to diagnose patients exhibiting cardiovascular disease symptoms or at risk for developing cardiovascular disease. In one embodiment, this assay is performed in a medical laboratory on a sample of peripheral blood, cells isolated from the peripheral blood, serum or plasma.

The diagnostic procedures can be performed "in situ" directly upon blood smears (fixed and/or frozen), or on tissue biopsies, such that no nucleic acid purification is necessary. DNA or RNA from a sample can be isolated using procedures which are well known to those in the art.

Nucleic acid reagents that are specific to the nucleic acid of interest, namely the nucleic acid encoding FOS or DUSP1, can be readily generated given the sequences of these genes for use as probes and/or primers for such in situ procedures (see, for example, Nuovo, G. J., 1992, *PCR in situ hybridization: protocols and applications*, Raven Press, NY).

A differential display procedure can be utilized based on Northern analysis and/or RT-PCR. An exemplary method is disclosed in the examples section below. In one embodiment, the methods disclosed herein include the use of an ordered array of nucleic acids representing thousands of genes on a solid support. mRNA from the cells of interest are used to create a labeled, first strand cDNA probe that is then hybridized to the microarray. In one embodiment, two mRNA samples are directly compared to the same microarray by incorporating different labels into the cDNA probes derived from the samples. The extent of hybridization of the probes to each nucleic acid sequence on the microarray is then quantitated and the ratio of the pixel intensities for each label is used as a measure of the relative mRNA expression in the two samples. In one embodiment, the array is an array of nucleic acids expressed by the immune system or the cardiovascular system.

In one example, a lymphochip is utilized, which includes nucleic acid sequences derived from high-throughput sequencing of cDNA clones from libraries of human immune cells. The array can incorporate, for example, thousands of clones from a library prepared from the immune system or the cardiovascular system. The array can also include genes of known structure and function based on their established role in immune cell differentiation, response and disorders. These types of arrays are well known in the art (see, for example, Staudt, *Trends Immunol.* 22:35-40, 2001; Staudt and Brown, *Ann. Rev. Immunol.* 18:829-859, 2000; Alizadeh et al., *Nature* 403:503-511, 2000; Alizadeh et al., *Cold Spring Harbor Symp. Quant. Biol.* 64:71-78, 1999; U.S. Patent Application No. 20030203416A1, all of which are incorporated herein by reference).

The array can be a high density array, such that the array includes greater than about 100, greater than about 1000, greater than about 16,000 and most greater than about 65,000 or 250,000 or even greater than about 1,000,000 different oligonucleotide probes. The oligonucleotide probes generally range from about 5 to about 50 nucleotides, such as about 10 to about 40 nucleotides in length or from about 15 to about 40 nucleotides in length.

The location and sequence of each different oligonucleotide probe sequence in the array is known. Moreover, in a high density array, the large number of different probes occupies a relatively small area so that there is a probe density of greater than about 60 different oligonucleotide probes per cm², such as greater than about 100, greater than about 600, greater than about 1000, greater than about 5,000, greater than about 10,000, greater than about 40,000, greater than about 100,000, or greater than about 400,000 different oligonucleotide probes per cm². The small surface area of the array (such as less than about 10 cm², less than about 5 cm², less than about 2 cm²) permits extremely uniform hybridization conditions (temperature regulation, salt content, etc.) while the extremely large number of probes allows parallel processing of hybridizations.

Generally, the methods of monitoring gene expression using array technology involve (1) providing a pool of target nucleic acids comprising RNA transcript(s) of one or more target gene(s), or nucleic acids derived from the RNA transcript(s); (2) hybridizing the nucleic acid sample to an array of probes (including control probes), that can be a high density array; and (3) detecting the hybridized nucleic acids and calculating a relative expression (transcription) level. In the present application, the expression of FOS and/or DUSP1 is evaluated.

In order to measure the transcription level of a gene or genes, it is desirable to provide a nucleic acid sample comprising mRNA transcript(s) of the gene or genes, or nucleic acids derived from the mRNA transcript(s). As used herein, a nucleic acid derived from an mRNA transcript refers to a nucleic acid for whose synthesis the mRNA transcript or a subsequence thereof has ultimately served as a template, such as a cDNA ("first strand" transcribed from the mRNA). Thus, a cDNA reverse transcribed from an mRNA, an RNA transcribed from that cDNA, a DNA amplified from the cDNA, an RNA transcribed from the amplified DNA, etc., are all derived from the mRNA transcript. Detection of such products is indicative of the presence and/or abundance of the original transcript in a sample. Thus, suitable samples include, but are not limited to, mRNA transcripts of the gene or genes, cDNA reverse transcribed from the mRNA, cRNA transcribed from the cDNA, and the like.

Generally, the transcription level (and thereby expression) of one or more genes in a sample is quantified, so that the nucleic acid sample is one in which the concentration of the mRNA transcript(s) of the gene or genes, or the concentration of the nucleic acids derived from the mRNA transcript(s), is proportional to the transcription level (and therefore expression level) of that gene. The hybridization signal intensity should also be proportional to the amount of hybridized nucleic acid. Generally, the proportionality is relatively strict (for example, a doubling in transcription rate results in approximately a doubling in mRNA transcript in the sample nucleic acid pool and a doubling in hybridization signal), one of skill will appreciate that the proportionality can be more relaxed and even non-linear. Thus, for example, an assay where a 5 fold difference in concentration of the target mRNA results in a 3 to 6 fold difference in hybridization intensity can be sufficient. Where more precise quantification is required, controls can be run to correct for variations introduced in sample preparation and hybridization as described herein. In addition, serial dilutions of "standard" target mRNAs can be used to prepare calibration curves according to methods well known to those of skill in the art. Of course, where simple detection of the presence or absence of a transcript (such as FOS and/or DUSP1) is desired, controls or calibrations may not be required.

In one embodiment, a nucleic acid sample is utilized, such as the total mRNA isolated from a biological sample. The biological sample can be from any biological tissue or fluid from the subject of interest, such as a subject who is suspected of having cardiovascular disease. Such samples include, but are not limited to, blood, blood cells (such as white blood cells) or tissue biopsies including vascular tissue. However, the sample could also be peritoneal fluid, and pleural fluid, cerebral spinal fluid, or cells separated from a sample.

Nucleic acids (such as mRNA) can be isolated from the sample according to any of a number of methods well known to those of skill in the art. Methods of isolating total mRNA are well known to those of skill in the art. For example, methods of isolation and purification of nucleic acids are described in detail in Chapter 3 of *Laboratory Techniques in Biochemistry and Molecular Biology: Hybridization With Nucleic Acid Probes, Part I. Theory and Nucleic Acid Preparation*, P. Tijssen, ed. Elsevier, N.Y. (1993) and Chapter 3 of *Laboratory Techniques in Biochemistry and Molecular Biology: Hybridization With Nucleic Acid Probes, Part I. Theory and Nucleic Acid Preparation*, P. Tijssen, ed. Elsevier, N.Y. (1993). In one example, the total nucleic acid is isolated from a given sample using, for example, an acid guanidinium-phenol-chloroform extraction method, and polyA+ mRNA is isolated by oligo dT column chromatography or by using (dT)n magnetic beads (see, for example, Sambrook et al. *Molecular Cloning: A Laboratory Manual* (2nd ed.), Vols. 1-3, Cold Spring Harbor Laboratory, (1989), or *Current Protocols in Molecular Biology*, F. Ausubel et al., ed. Greene Publishing and Wiley-Interscience, N.Y. (1987)). In another example, oligo-dT magnetic beads may be used to purify mRNA (Dynal Biotech Inc., Brown Deer, Wis.).

The nucleic acid sample can be amplified prior to hybridization. If a quantitative result is desired, a method is utilized that maintains or controls for the relative frequencies of the amplified nucleic acids. Methods of "quantitative" amplification are well known to those of skill in the art. For example, quantitative PCR involves simultaneously co-amplifying a known quantity of a control sequence using the same primers. This provides an internal standard that can be used to calibrate the PCR reaction. The array can then include probes specific to the internal standard for quantification of the amplified nucleic acid.

Suitable amplification methods include, but are not limited to, polymerase chain reaction (PCR) (see Innis et al., *PCR Protocols, A guide to Methods and Application*, Academic Press, Inc. San Diego, 1990), ligase chain reaction (LCR) (see Wu and Wallace, *Genomics* 4:560, 1989; Landegren et al., *Science* 241:1077, 1988; and Barringer, et al., *Gene* 89:117, 1990), transcription amplification (Kwoh et al., *Proc. Natl. Acad. Sci. U.S.A.* 86:1173, 1989), and self-sustained sequence replication (Guatelli et al., *Proc. Nat. Acad. Sci. U.S.A.* 87:1874, 1990). In one embodiment, the sample mRNA is reverse transcribed with a reverse transcriptase and a primer consisting of oligo dT and a sequence encoding the phage T7 promoter to provide single stranded DNA template (termed "first strand"). The second DNA strand is polymerized using a DNA polymerase. After synthesis of double-stranded cDNA, T7 RNA polymerase is added and RNA is transcribed from the cDNA template. Successive rounds of transcription from each single cDNA template results in amplified RNA.

Methods of in vitro polymerization are well known to those of skill in the art (see, for example, Sambrook, supra; Van Gelder et al., *Proc. Natl. Acad. Sci. U.S.A.* 87:1663-1667, 1990). The direct transcription method provides an antisense (aRNA) pool. Where antisense RNA is used as the target nucleic acid, the oligonucleotide probes provided in the array are chosen to be complementary to subsequences of the antisense nucleic acids. Conversely, where the target nucleic acid pool is a pool of sense nucleic acids, the oligonucleotide probes are selected to be complementary to subsequences of the sense nucleic acids. Finally, where the nucleic acid pool is double stranded, the probes may be of either sense as the target nucleic acids include both sense and antisense strands.

The protocols include methods of generating pools of either sense or antisense nucleic acids. Indeed, one approach can be used to generate either sense or antisense nucleic acids as desired. For example, the cDNA can be directionally cloned into a vector (for example Stratagene's pBluscript II KS (+) phagemid) such that it is flanked by the T3 and T7 promoters. In vitro transcription with the T3 polymerase will produce RNA of one sense (the sense depending on the orientation of the insert), while in vitro transcription with the T7 polymerase will produce RNA having the opposite sense. Other suitable cloning systems include phage lambda vectors designed for Cre-loxP plasmid subcloning (see, for example, Palazzolo et al., Gene 88:25-36, 1990).

In one embodiment, the nucleic acid from the tissue, peripheral blood, or other sample can be immobilized, for example, to a solid support such as a membrane, including nylon membranes or nitrocellulose, or a plastic surface such as that on a microtitre plate or polystyrene beads. Labeled nucleic acid probes that specifically bind FOS and/or DUSP1 are bound to the immobilized sample. The labels include radiolabels, enzymatic labels, and binding reagents (such as avidin or biotin). Detection of the annealed, labeled nucleic acid reagents is accomplished using standard techniques well known to those in the art.

In one embodiment, the hybridized nucleic acids are detected by detecting one or more labels attached to the sample nucleic acids. The labels can be incorporated by any of a number of methods. In one example, the label is simultaneously incorporated during the amplification step in the preparation of the sample nucleic acids. Thus, for example, polymerase chain reaction (PCR) with labeled primers or labeled nucleotides will provide a labeled amplification product. In one embodiment, transcription amplification, as described above, using a labeled nucleotide (such as fluorescein-labeled UTP and/or CTP) incorporates a label into the transcribed nucleic acids.

Alternatively, a label may be added directly to the original nucleic acid sample (such as mRNA, polyA mRNA, cDNA, etc.) or to the amplification product after the amplification is completed. Means of attaching labels to nucleic acids are well known to those of skill in the art and include, for example, nick translation or end-labeling (e.g. with a labeled RNA) by kinasing of the nucleic acid and subsequent attachment (ligation) of a nucleic acid linker joining the sample nucleic acid to a label (e.g., a fluorophore).

Detectable labels suitable for use include any composition detectable by spectroscopic, photochemical, biochemical, immunochemical, electrical, optical or chemical means. Useful labels include biotin for staining with labeled streptavidin conjugate, magnetic beads (for example DYNABEADS™), fluorescent dyes (for example, fluorescein, Texas red, rhodamine, green fluorescent protein, and the like), radiolabels (for example, $^3$H, $^{125}$I, $^{35}$S, $^{14}$C, or $^{32}$P), enzymes (for example, horseradish peroxidase, alkaline phosphatase and others commonly used in an ELISA), and colorimetric labels such as colloidal gold or colored glass or plastic (for example, polystyrene, polypropylene, latex, etc.) beads. Patents teaching the use of such labels include U.S. Pat. No. 3,817,837; U.S. Pat. No. 3,850,752; U.S. Pat. No. 3,939,350; U.S. Pat. No. 3,996,345; U.S. Pat. No. 4,277,437; U.S. Pat. No. 4,275,149; and U.S. Pat. No. 4,366,241.

Means of detecting such labels are also well known. Thus, for example, radiolabels may be detected using photographic film or scintillation counters, fluorescent markers may be detected using a photodetector to detect emitted light. Enzymatic labels are typically detected by providing the enzyme with a substrate and detecting the reaction product produced by the action of the enzyme on the substrate, and calorimetric labels are detected by simply visualizing the colored label.

The label may be added to the target (sample) nucleic acid(s) prior to, or after, the hybridization. So-called "direct labels" are detectable labels that are directly attached to or incorporated into the target (sample) nucleic acid prior to hybridization. In contrast, so-called "indirect labels" are joined to the hybrid duplex after hybridization. Often, the indirect label is attached to a binding moiety that has been attached to the target nucleic acid prior to the hybridization. Thus, for example, the target nucleic acid may be biotinylated before the hybridization. After hybridization, an avidin-conjugated fluorophore will bind the biotin bearing hybrid duplexes providing a label that is easily detected (see *Laboratory Techniques in Biochemistry and Molecular Biology*, Vol. 24: *Hybridization With Nucleic Acid Probes*, P. Tijssen, ed. Elsevier, N.Y., 1993).

Nucleic acid hybridization simply involves providing a denatured probe and target nucleic acid under conditions where the probe and its complementary target can form stable hybrid duplexes through complementary base pairing. The nucleic acids that do not form hybrid duplexes are then washed away leaving the hybridized nucleic acids to be detected, typically through detection of an attached detectable label. It is generally recognized that nucleic acids are denatured by increasing the temperature or decreasing the salt concentration of the buffer containing the nucleic acids. Under low stringency conditions (e.g., low temperature and/or high salt) hybrid duplexes (e.g., DNA:DNA, RNA:RNA, or RNA:DNA) will form even where the annealed sequences are not perfectly complementary. Thus, specificity of hybridization is reduced at lower stringency. Conversely, at higher stringency (e.g., higher temperature or lower salt) successful hybridization requires fewer mismatches.

One of skill in the art will appreciate that hybridization conditions can be designed to provide different degrees of stringency. In a one embodiment, hybridization is performed at low stringency in this case in 6×SSPE-T at 37° C. (0.005% Triton X-100) to ensure hybridization and then subsequent washes are performed at higher stringency (e.g., 1×SSPE-T at 37° C.) to eliminate mismatched hybrid duplexes. Successive washes may be performed at increasingly higher stringency (e.g., down to as low as 0.25×SSPE-T at 37° C. to 50° C.) until a desired level of hybridization specificity is obtained. Stringency can also be increased by addition of agents such as formamide. Hybridization specificity may be evaluated by comparison of hybridization to the test probes with hybridization to the various controls that can be present (e.g., expression level control, normalization control, mismatch controls, etc.).

In general, there is a tradeoff between hybridization specificity (stringency) and signal intensity. Thus, in one embodiment, the wash is performed at the highest stringency that produces consistent results and that provides a signal intensity greater than approximately 10% of the background intensity. Thus, the hybridized array may be washed at successively higher stringency solutions and read between each wash. Analysis of the data sets thus produced will reveal a wash stringency above which the hybridization pattern is not appreciably altered and which provides adequate signal for the particular oligonucleotide probes of interest. These steps have been standardized for commercially available array systems.

Methods for evaluating the hybridization results vary with the nature of the specific probe nucleic acids used as well as the controls provided. In one embodiment, simple quantification of the fluorescence intensity for each probe is determined. This is accomplished simply by measuring probe signal strength at each location (representing a different probe) on the array (for example, where the label is a fluorescent label, detection of the amount of florescence (intensity) produced by a fixed excitation illumination at each location on the array). Comparison of the absolute intensities of an array hybridized to nucleic acids from a "test" sample (such as from a patient treated with a therapeutic protocol) with intensities produced by a "control" sample (such as from the same patient prior to treatment with the therapeutic protocol) provides a measure of the relative expression of the nucleic acids that hybridize to each of the probes.

Changes in expression detected by these methods for instance can be different for different therapies, and may include increases or decreases in the level (amount) or functional activity of such nucleic acids, their expression or translation into protein, or in their localization or stability. An increase or a decrease can be, for example, about a 1-fold, 2-fold, 3-fold, 4-fold, 5-fold, change (increase or decrease) in the expression of a particular nucleic acid, such as a nucleic acid encoding FOS and/or DUSP1.

Certain of the encompassed methods involve measuring an amount of the molecule in a sample that includes monocytes (such as a serum, blood or tissue sample) derived or taken from the subject, in which a difference (an increase or a decrease) in the level of the molecule relative to that present in a sample derived or taken from the subject at an earlier time, is diagnostic for atherosclerosis or prognostic for the usefulness of the specific therapeutic protocol. Certain of the encompassed methods involve measuring an amount of a molecule in a sample derived or taken from the subject, compared to the level of the molecule relative to that present in a control sample, such as a subject that correctly responds, or does not respond, to the therapeutic protocol of interest. Although this can be accomplished using nucleic acid arrays, it does not require the use of such a nucleic acid array.

Alterations, including increases or decreases in the expression of nucleic acid molecules can be detected using, for instance, in vitro nucleic acid amplification and/or nucleic acid hybridization. The results of such detection methods can be quantified, for instance by determining the amount of hybridization or the amount of amplification.

Detection of FOS and DUSP1 Polypeptides

In several embodiment, an amount of FOS and/or DUSP1 polypeptides are measured. This can be accomplished using immunoassays or using spectrometric methods. The expression of FOS and/or DUSP1 can be prepared to a control. One of skill in the art can readily identify an appropriate control, such as a sample from a subject known not to have a disorder (a negative control), a sample from a subject known to have a disorder (a positive control), or a known amount of FOS and/or DUSP1 polypeptide (a standard or a normal level found in a healthy subject). Statistically normal levels of FOS and/or DUSP1 polypeptide can be determined for example, from a subject with known not be have atherosclerosis, and to at low risk for a cardiac event. In one non-limiting example, normal levels can be assessed by measuring FOS and/or DUSP1 in the blood, serum, or plasma of young adults, who do not smoke or drink, exercise regularly, have no known history of cardiac events, and no familial history of heart disease.

Both monoclonal and polyclonal antibodies, and fragments thereof, can also be utilized to detect and quantify the expression of FOS and/or DUSP1. This can be accomplished, for example, by immunohistochemistry, immunoassay (such as enzyme-linked immunosorbent assay (ELISA) or radioimmunoassay (RIA)), Western blotting, flow cytometric or fluorimetric detection. The antibodies (or fragments thereof) can be employed histologically, as in immunofluorescence or immunoelectron microscopy, for in situ detection of FOS and/or DUSP1. In situ detection includes contacting a histological specimen from a subject with labeled antibody, and detecting binding of the antibody to monocytes within the sample. A wide variety of histological methods (such as staining procedures) can be modified in order to achieve such in situ detection.

Generally, immunoassays for FOS and DUSP1 typically include incubating a biological sample including monocytes, such as a biological fluid, a tissue extract, or freshly harvested cells, in the presence of antibody, and detecting the bound antibody by any of a number of techniques well known in the art. The biological sample can be blood, serum or plasma. The biological sample can also be isolated monocytes. The biological sample can be brought in contact with and immobilized onto a solid phase support or carrier such as nitrocellulose, or other solid support which is capable of immobilizing cells, cell particles or soluble proteins. The support may then be washed with suitable buffers followed by treatment with the antibody that binds FOS and or the antibody that binds DUSP1. The solid phase support can then be washed with the buffer a second time to remove unbound antibody. If the antibody is directly labeled, the amount of bound label on solid support can then be detected by conventional means. If the antibody is unlabeled, a labeled second antibody, which detects that antibody that specifically binds FOS and/or the antibody can be used.

By "solid phase support or carrier" is intended any support capable of binding an antigen or an antibody. Well-known supports or carriers include glass, polystyrene, polypropylene, polyethylene, dextran, nylon, amylases, natural and modified celluloses, polyacrylamides, gabbros and magnetite. The nature of the carrier can be either soluble to some extent or insoluble for the purposes of the present disclosure. The support material may have virtually any possible structural configuration so long as the coupled molecule is capable of binding to an antigen or antibody. Thus, the support configuration may be spherical, as in a bead, or cylindrical, as in the inside surface of a test tube, or the external surface of a rod. Alternatively, the surface may be flat such as a sheet or test strip.

In one embodiment, proteins are isolated from a sample including monocytes, such as a peripheral blood sample. In other embodiments, proteins are isolated from serum or plasma. In one embodiment, an enzyme linked immunosorbent assay (ELISA) is utilized to detect the protein (Voller, "The Enzyme Linked Immunosorbent Assay (ELISA)," *Diagnostic Horizons* 2:1-7, 1978, Microbiological Associates Quarterly Publication, Walkersville, Md.; Voller et al., *J. Clin. Pathol.* 31:507-520, 1978; Butler, *Meth. Enzymol.* 73:482-523, 1981; Maggio, (ed.) *Enzyme Immunoassay*, CRC Press, Boca Raton, Fla., 1980; Ishikawa, et al., (eds.) *Enzyme Immunoassay*, Kgaku Shoin, Tokyo, 1981). In this method, an enzyme which is bound to the antibody will react with an appropriate substrate, preferably a chromogenic substrate, in such a manner as to produce a chemical moiety which can be detected, for example, by spectrophotometric, fluorimetric or by visual means. Enzymes which can be used to detectably label the antibody include, but are not limited to, malate dehydrogenase, staphylococcal nuclease, delta-5-steroid isomerase, yeast alcohol dehydrogenase, alpha-glycerophosphate, dehydrogenase, triose phosphate isomerase, horseradish peroxidase, alkaline phosphatase, asparaginase, glucose oxidase, beta-galactosidase, ribonuclease, urease, catalase, glucose-6-phosphate dehydrogenase, glucoamylase and acetylcholinesterase. The detection can be accomplished by colorimetric methods which employ a chromogenic substrate for the enzyme. Detection can also be accomplished by visual comparison of the extent of enzymatic reaction of a substrate in comparison with similarly prepared standards.

However, detection can also be accomplished using any of a variety of other immunoassays. For example, by radioactively labeling the antibodies or antibody fragments, it is possible to detect fingerprint gene wild-type or mutant peptides through the use of a radioimmunoassay (RIA) (see, for example, Weintraub, B., *Principles of Radioimmunoassays, Seventh Training Course on Radioligand Assay Techniques*, The Endocrine Society, March, 1986, which is incorporated by reference herein). In another example, a sensitive and specific tandem immunoradiometric assay may be used (see Shen and Tai, *J. Biol. Chem.*, 261:25, 11585-11591, 1986). The radioactive isotope can be detected by such means as the use of a gamma counter or a scintillation counter or by autoradiography.

It is also possible to label the antibody with a fluorescent compound. When the fluorescently labeled antibody is exposed to light of the proper wavelength, its presence can then be detected due to fluorescence. Among the most commonly used fluorescent labeling compounds are fluorescein isothiocyanate, rhodamine, phycoerythrin, phycocyanin, allophycocyanin, o-phthaldehyde and fluorescamine. The antibody can also be detectably labeled using fluorescence emitting metals such as $^{152}$Eu, or others of the lanthanide series. These metals can be attached to the antibody using such metal chelating groups as diethylenetriaminepentacetic acid (DTPA) or ethylenediaminetetraacetic acid (EDTA). The antibody also can be detectably labeled by coupling it to a chemiluminescent compound. The presence of the chemiluminescent-tagged antibody is then determined by detecting the presence of luminescence that arises during the course of a chemical reaction. Examples of particularly useful chemiluminescent labeling compounds are luminol, isoluminol, theromatic acridinium ester, imidazole, acridinium salt and oxalate ester. Likewise, a bioluminescent compound can be used to label the antibody of the present invention. Bioluminescence is a type of chemiluminescence found in biological systems in which a catalytic protein increases the efficiency of the chemiluminescent reaction. The presence of a bioluminescent protein is determined by detecting the presence of luminescence. Important bioluminescent compounds for purposes of labeling are luciferin, luciferase and aequorin.

Any method known to those of skill in the art can be used to detect and quantify FOS and/or DUSP1 protein. Thus, in additional embodiments, a spectrometric method is utilized. Spectrometric methods include mass spectrometry, nuclear magnetic resonance spectrometry, and combinations thereof. In one example, mass spectrometry is used to detect the presence of FOS and/or DUSP1 protein in a biological sample, such as a blood sample, a serum sample, or a plasma sample (see for example, Stemmann, et al., *Cell* December 14; 107(6):715-26, 2001; Zhukov et al., "From Isolation to Identification: Using Surface Plasmon Resonance-Mass Spectrometry in Proteomics, PharmaGenomics, March/April 2002, available on the PharmaGenomics website on the internet).

Screening for Agents of Use in the Treatment of Atherosclerosis

A method is provided herein for selecting an agent that is of use in the treatment of atherosclerosis. The method includes contacting monocytes with the test compound of interest, and evaluating the expression of FOS, the expression of DUSP1, or the expression of both FOS and DUSP1.

The monocytes can be in vitro. In one embodiment, the monocytes can be cells from a monocyte cell line, including human and non-human cells. Specific examples of monocyte cell lines are THP-1, U937, HL-60, K562, MonoMac6, J774A.1, RAW 264.7, and LADMAC. In another embodiment, the monocytes can also be peripheral blood monocytes from a subject. In one embodiment, peripheral blood monocytes are isolated from the other blood components.

The monocytes can also be in vivo. In one example, a therapeutically effective amount of a pharmaceutical agent of interest is administered to a subject. A sample including monocytes is taken from the subject, and the expression of FOS, DUSP1, or both FOS and DUSP1 is assessed. For example, the sample can be peripheral blood.

The expression of FOS, DUSP1, or both FOS and DUSP1, can be compared to a control. One of skill in the art can readily identify an appropriate control, such as a sample from a subject known not to have a disorder (a negative control), a sample from a subject known to have a disorder (a positive control), or a known amount of nucleic acid encoding FOS and/or DUSP1 (a standard or a normal level found in a healthy subject). Statistically normal levels can be determined for example, from a subject with known not be have atherosclerosis, and to at low risk for a cardiac event. In one non-limiting example, normal levels can be assessed by measuring FOS and/or DUSP1 in the blood, serum, or plasma of young adults, who do not smoke or drink, exercise regularly, have no known history of cardiac events, and no familial history of heart disease. Suitable controls also include a standard value, the level of FOS and/or DUSP1 in monocytes not contacted with the agent, and the level of FOS and/or DUSP1 is a sample from a subject not administered the test agent or administered only the carrier for the test agent, such as a buffer The test agent can be any compound of interest, including chemical compounds, small molecules, polypeptides or other biological agents (for example antibodies or cytokines). In several examples, a panel of potential agents is screened, such as a panel of cytokines, pharmaceutical agents (such as statins) or growth factors is screened.

Methods for preparing a combinatorial library of molecules that can be tested for a desired activity are well known in the art and include, for example, methods of making a phage display library of peptides, which can be constrained peptides (see, for example, U.S. Pat. No. 5,622,699; U.S. Pat. No. 5,206,347; Scott and Smith, *Science* 249:386-390, 1992; Markland et al., *Gene* 109:13-19, 1991), a peptide library (U.S. Pat. No. 5,264,563); a peptidomimetic library (Blondelle et al., *Trends Anal Chem.* 14:83-92, 1995); a nucleic acid library (O'Connell et al., *Proc. Natl. Acad. Sci. U.S.A.* 93:5883-5887, 1996; Tuerk and Gold, *Science* 249: 505-510, 1990; Gold et al., *Ann. Rev. Biochem.* 64:763-797, 1995); an oligosaccharide library (York et al., *Carb. Res.* 285:99-128, 1996; Liang et al., *Science* 274:1520-1522, 1996; Ding et al., *Adv. Expt. Med. Biol.* 376:261-269, 1995); a lipoprotein library (de Kruif et al., *FEBS Lett.* 399:232-236, 1996); a glycoprotein or glycolipid library (Karaoglu et al., *J Cell Biol.* 130:567-577, 1995); or a chemical library containing, for example, drugs or other pharmaceutical agents (Gordon et al., *J Med. Chem.* 37:1385-1401, 1994; Ecker and Crooke, *BioTechnology* 13:351-360, 1995). Polynucleotides can be particularly useful as agents that can alter a function of ES cells because nucleic acid molecules having binding specificity for cellular targets, including cellular polypeptides, exist naturally, and because synthetic molecules having such specificity can be readily prepared and identified (see, for example, U.S. Pat. No. 5,750,342).

In one embodiment, for a high throughput format, monocytes can be introduced into wells of a multiwell plate or of a glass slide or microchip, and can be contacted with the test agent. Generally, the cells are organized in an array, particularly an addressable array, such that robotics conveniently can be used for manipulating the cells and solutions and for monitoring the monocytes, particularly with respect to the function being examined. An advantage of using a high throughput format is that a number of test agents can be examined in parallel, and, if desired, control reactions also can be run under identical conditions as the test conditions. As such, the methods disclosed herein provide a means to screen one, a few, or a large number of test agents in order to identify an agent that can alter a function of monocytes, for example, an agent that alters FOS expression, DUSP1 expression or both. In one embodiment, an agent is identified that decreases FOS expression, DUSP1 expression, or both, as compared to a control. The decrease can be, for example, at least about 30%, such as at least about 50%, such as at least about 55%, at least about 70%, at least about 75%, at least about 80%, at least about 85% or at least about 90%. The control can be a standard value, a cell not contacted with the agent, a cell contacted with an agent known to affect the expression of FOS, DUSP1, or both, or a cell contacted with a pharmaceutical carrier, or a cell contacted with an agent known not to affect the expression of FOS, DUSP1, or both.

The cells are contacted with test compounds sufficient for the compound to interact with the cell. When the compound binds a discrete receptor, the cells are contacted for a sufficient time for the agent to bind its receptor. In some embodiments, the cells are incubated with the test compound for an amount of time sufficient to affect phosphorylation of a substrate. In some embodiments, cells are treated in vitro with test compounds at 37° C. in a 5% $CO_2$ humidified atmosphere. Following treatment with test compounds, cells are washed with $Ca^{2+}$ and $Mg^{2+}$ free PBS and total protein is extracted as described (Haldar et al., *Cell Death Diff.* 1:109-115, 1994; Haldar et al., *Nature* 342:195-198, 1989; Haldar et al., *Cancer Res.* 54:2095-2097, 1994). In additional embodiments, serial dilutions of test compound are used.

Methods of Treatment of Atherosclerosis

Methods are disclosed herein for improving vascular function in a subject. The methods include administering to the subject a therapeutically effective amount of an agent identified using the methods disclosed herein to treat a disorder in a subject. In one embodiment, the subject has atherosclerosis. In other embodiments, the subject has had a myocardial infarction, or has intermittent claudication, bowel ischemia, retinal ischemia, transient ischemic attacks (TIAs), ischemic strokes, restenosis after angioplasty, transplant atherosclerosis, unstable angina, or another condition associated with cardiovascular dysfunction.

An agent is identified using the methods disclosed herein, and a therapeutically effective dose is determined by various methods, including generating an empirical dose-response curve, predicting potency and efficacy of using modeling, and other methods used in the biological sciences. In general, a therapeutically effective amount of the agent is an amount sufficient to prevent, treat, reduce, eliminate and/or ameliorate a symptom and/or the underlying causes of the disease or disorder being treated, such as any condition associated with cardiovascular dysfunction. In one embodiment, a therapeutically effective amount is an amount sufficient to treat atherosclerosis, or to lower cholesterol. The therapeutically effective amount will be dependent on the subject being treated (e.g. the species or size of the subject), the type of cardiovascular dysfunction suffered by the subject, and the location of administration of the agent (e.g. intravenously, locally, etc). One or multiple doses can be administered. Administration can be systemic or local, and can be by any route, such as intramuscular, subcutaneous, intravascular, intraperitoneal, intranasal, or oral administration. Administration can be by injection. Specific, non-limiting examples of administration by injection include administration by subcutaneous injection, intramuscular injection, or intravenous injection. If administration is intravenous, an injectable liquid suspension of endothelial progenitor cells can be prepared and administered by a continuous drip or as a bolus. The therapeutically effective amount can be administered in conjunction with another agent, such as a statin or an agent that affects monocyte function.

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. Similarly, the word "or" is intended to include "and" unless the context clearly indicates otherwise. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of this disclosure, suitable methods and materials are described below. The term "comprises" means "includes." All publications, patent applications, patents, and other references mentioned herein are incorporated by reference in their entirety. In case of conflict, the present specification, including explanations of terms, will control. In addition, the materials, methods, and examples are illustrative only and not intended to be limiting.

The disclosure is illustrated by the following non-limiting Examples.

EXAMPLES

The importance of inflammation in atherosclerosis has become well established as evidenced by the clinical use of inflammatory markers such as high-sensitivity C-reactive protein (hsCRP) for cardiac risk stratification (Libby et al., *Circulation* 105(9):1135-1143, 2002; Ross, *N Engl J Med* 340(2):115-126, 1999). With increasing lifespan and prevalence of cardiac risk factors such as obesity and the metabolic syndrome, the discovery of new biomarkers and therapeutic targets can help improve the management of this disease commonly associated with aging and insulin resistance.

Cardiovascular investigators have been limited by a number of factors such as difficulty in obtaining diseased tissue, functional complexity of the system, and lack of in vitro human disease models. The variety of blood cells which circulate throughout the body present an ideal tissue for atherosclerosis studies for four reasons: 1) they are easily accessible and include inflammatory cells such as monocytes which are critical elements in the atherosclerotic process; 2) circulating blood cells are in intermittent intimate contact with the diseased endovascular lumen and as such may serve as reporters; 3) blood cells have defined cell surface markers facilitating their purification to homogeneity; 4) there are immortalized human monocytic cell lines, which retain differentiated phenotypes, and can thus support in vitro studies.

To identify disease markers and genes involved in pathogenesis, gene expression was quantified in circulating monocytes from patients with atherosclerosis and compared the results to those of normal subjects using the serial analysis of gene expression (SAGE) technique (Polyak et al., *J Clin Oncol* 19(11):2948-2958, 2001; Saha et al., *Nat Biotechnol* 20(5):508-512, 2002; Patino et al., *Circ Res* 91(7):565-569, 2002, which are all incorporated by reference herein). The analyses presented herein revealed higher levels of various stress response and inflammatory gene transcripts in the monocytes of patients compared to normal controls, and one in particular, FOS, was strongly expressed in the circulating monocytes of patients. In comparison to plasma hsCRP, elevated FOS transcript levels were more significantly associated with patients who had severe atherosclerosis that required coronary revascularization. FOS was initially identified as the transforming activity of a murine osteosarcoma virus, and the human homolog of this viral oncogene has subsequently been well characterized (Finkel et al., *Science* 151(711):698-701, 1966; Ransone et al., *Annu Rev Cell Biol* 6:539-557, 1990). Though FOS has been studied in myeloid cell differentiation and activation, its role in monocytes and atherosclerosis is demonstrated herein with complementary clinical and basic experimental data showing that FOS is a marker and mediator of atherosclerosis.

Example 1

Materials and Methods

The following material and methods were used in the experiments disclosed herein:

Human subjects: All patients and normal volunteers were recruited after informed consent. The patients were selected from those scheduled to undergo carotid endarterectomy for atherosclerotic disease according to standard surgical guidelines. The normal control subjects were screened to ensure absence of significant atherosclerosis based on history and physical examination, electrocardiogram, echocardiogram, exercise stress testing and carotid artery ultrasonogram with intima-media thickness (IMT) measurements. The exclusions criteria for all subjects were: history of chronic infections, vasculitis or any other inflammatory disease, neoplastic disease, immunosuppressive therapy and chemotherapy.

Blood purification: Blood samples were collected from controls and from patients intraoperatively and processed within 1 hour of collection as previously described (Holodniy et al., *J Clin Microbiol* 33(6):1562-1566, 1995). Blood samples were collected into Vacutainer CPT tubes (Becton Dickinson, Franklin Lakes, N.J.) containing sodium citrate and Ficoll Hypaque gradient with a gel barrier that allowed a one-step isolation of mononuclear cells (MNC) then subsequently processed at 4° C. MNCs were resuspended in RNA Lysis/Binding buffer (Dynal Biotech Inc. Brown Deer, Wis.) for RT-PCR as described below. Monocytes were obtained by double column purification using CD14 MicroBeads and Fc Blocking reagent according to protocol (Miltenyi Biotec, Auburn, Calif.). Cell counts and viability were determined by Trypan Blue exclusion (>95%) and purity determined by flow-cytometry (>95% CD14+) and RT-PCR (FIGS. 4A-B).

Macrophage purification: Within one hour of surgical resection, human carotid artery plaques were processed as described with the following modifications (St. Croix et al., *Science* 289(5482):1197-1202, 2000; Liu-Wu et al., *Cytometry* 29(2):155-164, 1997). The tissue was rinsed, cut into fine 0.5 mm cubes and digested in Hank's Balanced Salt Solution (HBSS, HEPES 4.8 mg/ml) containing collagenase type IV (450 units/ml), DNase I (500 units/ml) and trypsin inhibitor (1 mg/ml) (Worthington Bichemical Co., Lakewood, N.J.) for 30 minutes to 1 hour at 37° C. The resulting cell suspension was sequentially filtered through 600 to 40 μm nylon filters (Spectrum Laboratories, Inc., Rancho Dominguez, Calif.) and macrophages isolated using CD14 Microbeads as described for the monocytes. Cell viability was greater than 95% by Trypan Blue exclusion. Macrophage purity was determined by CD14+ immunoreactivity (>90%) and by RT-PCR (FIG. 4B).

Mice and splenocytes: C57BL/6J ApoE gene knockout mice (at least 10 generation backcrossed, Jackson Laboratory, Bar Harbor, Me.) were maintained on normal chow (4.5% fat) per animal care guidelines. At age 17-21 week mice were sacrificed and their spleens placed in ice-cold RPMI media, gently ground and filtered through a 40 μm filter and erythrocytes lysed in cold ACK buffer (Bio-Whittaker, Walkersville, Md.). Purified splenocytes (25-50×10$^6$ cells per animal) with greater than 80% viability were resuspended in RNA lysis buffer.

Cell lines and tissue culture: All human monocytic cell lines were obtained from the American Type Culture Collection (Manassas, Va.) and maintained per protocol. The MonoMac6 cell line has been described (Ziegler-Heitbrock et al., *Int J Cancer* 41(3):456-461, 1988).

SAGE: SAGE libraries were made according to the Long-SAGE protocol (Saha et al., *Nat Biotechnol* 20(5):508-512, 2002). A SpectruMedix 192-capillary automated sequencer (SpectruMedix, State College, Pa.) was used for sequencing 50,000 to 100,000 tags per library. SAGE tags were counted using the SAGE2000 software (see the sagenet website, available online) normalized to 100,000 tags per library and identified using the Unigene/SAGEmap database (Lash et al., *Genome Res* 10(7):1051-1060, 2000). Tags matching a single Unigene cluster were summed and fold-change/total tag queries were performed using Microsoft Access.

Quantitative real-time RT-PCR: mRNA from lystates (10$^5$ cells) were purified by binding to poly(dT) magnetic beads (Dynal Biotech Inc. Brown Deer, Wis.) and reverse transcribed using Superscript II (Invitrogen, Carlsbad, Calif.). All primer sequences for the various genes are provided in Table 1. Standard quantitative RT-PCR was performed in duplicates at least two to three times using SYBR Green (Molecular Probes, Eugene, Oreg.) and TaqMan protocols on the 7900HT Sequence Detection System (Applied Biosystems, Inc., Foster City, Calif.) (Cerutti et al., *J Clin Invest* 113(8):1234-1242, 2004). RT-PCR data were normalized by measuring average cycle threshold (Ct) ratios between candidate genes and two different control genes, eukaryotic translation initiation factor (EIF3S5 or TIF) and GAPD. The formula $2^{Ct(Candidate)}/2^{Ct(Control)}$ was used to calculate normalized ratios. Color-coded normalized fold changes were generated from log transformed control-normalized ratios (normalized Ct ratio divided by the average Ct ratio of all control samples) using Cluster v2.2 and Treeview Software (available online through the Rana/Eisen Software website, maintained by the U.S. government (Cerutti et al., *J Clin Invest* 113(8):1234-1242, 2004).

The primer sequences are listed below.

TABLE 1

RT-PCR primer sequences

| Gene | Forward (5'-3') | Reverse (5'-3') |
|---|---|---|
| Human | | |
| GAPD | CATCTCTGCCCCCTCTGCT (SEQ ID NO: 1) | ACGCCTGCTTCACCACCTT (SEQ ID NO: 2) |
| TIF | GACACAAGTCTCCAGAACGGC (SEQ ID NO: 3) | TGGTCTCAAAGTCATCGGGAA (SEQ ID NO: 4) |
| FOS | GGAGGACCTTATCTGTGCGTGA (SEQ ID NO: 5) | GAACACACTATTGCCAGGAACACA (SEQ ID NO: 6) |
| DUSP1 | GGAGGACAACCACAAGGCAGA (SEQ ID NO: 7) | TGTGTCGTCGGGAATAATACTGGT (SEQ ID NO: 8) |
| NFKBIA | TACGAGCAGATGGTCAAGGAGC (SEQ ID NO: 9) | TTCAGGATGGAGTGGAGGTGC (SEQ ID NO: 10) |
| ID2 | CCCAGAACAAGAAGGTGAGCAA (SEQ ID NO: 11) | CAAGTAAGAGAACACCCTGGGAAG (SEQ ID NO: 12) |
| PER1 | TCCAGTCCAGCCTTACCTACAGC (SEQ ID NO: 13) | CCAACCCTCAAGAGTCAGATTCAG (SEQ ID NO: 14) |
| SAP30 | GCATCTCCCAGAAGAAGGTGAAG (SEQ ID NO: 15) | TAAGTCCTGGTCTGGTTGGTAGC (SEQ ID NO: 16) |
| CD14 | TCCGAAGCCTTCCAGTGTGT (SEQ ID NO: 17) | ACAGAGAGCCGCCATCAGTC (SEQ ID NO: 18) |
| CD206 | TGGTTTCCATTGAAAGTGCTGC (SEQ ID NO: 19) | TTCCTGGGCTTGACTGACTGTTA (SEQ ID NO: 20) |
| CD3 | TTCCCAACCCAGACTATGAGC (SEQ ID NO: 21) | AAGGAGGGAACTGAACGGAG (SEQ ID NO: 22) |
| GPIIb | ACAGATCTTCCTGCCAGAGC (SEQ ID NO: 23) | CACCCACCAGATTGGAATGGC (SEQ ID NO: 24) |
| Mouse | | |
| TIF | CTGAGGATGTGCTGTCTGGGAA (SEQ ID NO: 25) | CCTTTGCCTCCACTTCGGTC (SEQ ID NO: 26) |
| FOS | TGGAGCCAGTCAAGAGCATCA (SEQ ID NO: 27) | GGTAGGTGAAGACAAAGGAAGACG (SEQ ID NO: 28) |
| DUSP1 | TTTGAGTTTGTGAAGCAGAGGCG (SEQ ID NO: 29) | CAAGCGAAGAAACTGCCTCAAACA (SEQ ID NO: 30) |

Gene primer pair sequences used for the various quantitative RT-PCR reactions. Full gene names appear in the corresponding figure legends where the primer pairs were utilized.

Immunohistochemistry and western blotting: Antibodies: rabbit polyclonal anti-FOS (Santa Cruz Biotechnology, Santa Cruz, Calif.), mouse monoclonal anti-human CD14 (Immunotech, Marseille, France), mouse monoclonal anti-GAPD (Ambion, Austin, Tex.), and negative control mouse IgG (Biocare, Walnut Creek, Calif.). Serial cryosections (8-10 μm) of carotid plaques were immunostained with Vector Blue substrate (Vector laboratories, Inc., Burlingame, Calif.) developed by secondary antibody conjugated to alkaline phosphatase (Yu et al., *Mol Cell* 7(3):673-682, 2001). Western-blotting was done as previously described (Audic et al., *Genome Res* 7(10):986-995, 1997).

Plasma CRP measurements: Plasma high sensitivity C-reactive protein levels were determined using a solid phase enzyme-linked immunosorbent assay per protocol (Bio-Check, Inc., Burlingame, Calif.). To ensure accuracy, all samples were re-measured and validated by an external laboratory (Quest Diagnostics, Inc., Baltimore, Md.).

FOS inhibition by siRNA: Non-specific and FOS siRNA duplexes were purchased from Dharmacon Research (Lafayette, Colo.). FOS siRNA target sequences: 5'-GGG AUA GCC UCU CUU ACU A-3' (SEQ ID NO: 31), 5'-GAA CAG UUA UCU CCA GAA G-3' (SEQ ID NO: 32), 5'-GGA GAC AGA CCA ACU AGA A-3' (SEQ ID NO: 33), 5'-AGA CCG AGC CCU UUG AUG A-3' (SEQ ID NO: 34). 600 pmoles of siRNA were transiently transfected into $1 \times 10^6$ cells in 100 μl of Nucleofector Solution V according to the manufacturer's protocol (Amaxa Inc., Gaithersburg, Md.).

Monocyte function: For pretreatment experiments, cells were incubated with 10 μM simvastatin and/or 1 mM mevalonate for 20 hours prior to stimulation with phorbol 12-myristate 13-acetate (PMA, Sigma, St. Louis, Mo.). Cell adhesion was determined by gently washing off the nonadherent cells twice and pooling them. The remaining adherent cells were released with trypsin-EDTA (Invitrogen, Carlsbad, Calif.). Viable nonadherent and adherent cells were counted using Trypan Blue dye. Cumulative MCP-1 release into the medium was determined using the MCP-1 immunoassay kit (R& D Systems, Minneapolis, Minn.) after 24 hours PMA stimulation.

Statistical analysis: Data are expressed as mean±standard error (SE). P values were calculated with the use of a two-tailed Student's t-test. P values for SAGE tag counts were calculated accounting for sample size differences between libraries as previously described (Audic et al., *Genome Res* 7(10):986-995, 1997).

Example 2

Serial Analysis of Gene Expression

An adaptation of SAGE was utilized that greatly increases the specificity of this sequencing-based gene expression technique (Saha et al., *Nat Biotechnol* 20(5):508-512, 2002; Velculescu et al., *Trends Genet* 16(10):423-425, 2000). The quantitative nature of SAGE simplifies data analyses with minimal normalization requirements. The strategy of creating a limited number of SAGE libraries was used, wherein purified CD14+ monocytes were used to screen for monocyte-specific candidate genes. This was followed by higher throughput quantitative reverse-transcription PCR RT-PCR) using mononuclear cells to efficiently confirm candidate genes in larger groups of subjects.

A total of seven SAGE libraries were made. Five CD14+ monocytes libraries were made as follows: two from carotid endarterectomy (CEA) patients (P1, P2); one from an age-matched normal control (C1); and two from younger subjects (A1, A2) to exclude age-related changes and to serve as additional controls (subject selection details in Methods) (Table 2).

TABLE 2

Table 2 Subjects[1]

| | SAGE subjects | | | | | RT-PCR confirmation subjects | |
|---|---|---|---|---|---|---|---|
| | P1 | P2 | C1 | A1 | A2 | Controls (n = 19) | Patients (n = 25) |
| Age (yr) | 71 | 72 | 68 | 45 | 39 | 70 ± 5 | 74 ± 8 |
| Gender | M | F | F | M | M | 42% Male | 60% Male |
| Systolic blood pressure (mm Hg) | 134 | 120 | 145 | 130 | 115 | 141 ± 18 | 143 ± 20 |
| LDL (mg/dl) | 101 | 100 | 65 | 87 | 124 | 110 ± 33 | 103 ± 28 |
| HDL (mg/dl) | 44 | 66 | 48 | 55 | 47 | 56 ± 21 | 53 ± 16 |
| Diabetes mellitus | − | − | − | − | − | 5% | 8% |
| Current smoker | − | − | − | − | − | 0% | 4% |
| Family history of CHD | − | + | − | − | − | 36% | 48% |
| History of CHD | + | + | − | − | − | 5% | 56% |
| Body Mass Index (kg/m$^2$) | 29.2 | 27.7 | 28.0 | 25.6 | 23.0 | 26.3 ± 3.8 | 26.4 ± 4.9 |
| Framingham 10-year CHD risk (%) | 18 | 8 | 9 | 3 | 3 | 13 ± 9 | 15 ± 10 |

[1]Individual profiles of the subjects used for SAGE library construction and group profiles of normal subjects (Controls) and carotid endarterectomy patients (Patients) used for quantitative RT-PCR. Patient 1 (P1), patient 2 (P2), age-matched control 1 (C1), younger age control 1 (A1), younger age control 2 (A2), coronary heart disease (CHD).

Two monocyte-depleted mononuclear (non-monocyte) cell libraries were made from subjects P1 and A1 for screening out candidate genes also expressed in non-monocytes.

A total of 460,012 SAGE tags, or an estimated 2-3 fold redundant coverage of the transcriptome, from the five monocyte SAGE libraries (P1, P2, C1, A1, A2) were sequenced and matched to 13,154 genes in the Unigene database. Based on known tags expressed on average at least two tags per library, the pairwise correlation coefficients between monocyte libraries were very high, 0.9992±0.0004. As expected of monocytes purified using the CD14 surface antigen, CD14 transcripts were greatly enriched as were other monocyte markers such as CD163 (Table 3). In contrast, the non-monocyte SAGE libraries, mostly composed of lymphocytes, were enriched in T- and B-cell markers such as CD3E and CD79A, respectively (Table 3).

TABLE 3

SAGE libraries

| | | | Normalized SAGE tag counts | | | | | |
|---|---|---|---|---|---|---|---|---|
| | | Unigene | Monocyte | | | | Non-monocyte | |
| Gene description | SAGE tag sequence | ID | P1 | P2 | C1 | A1 | A2 | P1 | A1 |
| Hematopoietic markers Monocyte | | | | | | | | | |
| CD14 antigen | TGGTGCAGCGCCCTGAA (SEQ ID NO: 35) | 163867 | 53 | 70 | 107 | 113 | 78 | 4 | 0 |

TABLE 3-continued

SAGE libraries

| Gene description | SAGE tag sequence | Unigene ID | Normalized SAGE tag counts |  |  |  |  |  |  |
|---|---|---|---|---|---|---|---|---|---|
| | | | Monocyte | | | | | Non-monocyte | |
| | | | P1 | P2 | | C1 | A1 | A2 | P1 | A1 |
| CD163 antigen | GAGGTTCCTGGGGGACA (SEQ ID NO: 36) | 74076 | 27 | 38 | | 24 | 14 | 21 | 0 | 0 |
| Non-monocyte | | | | | | | | | | |
| CD3E antigen, epsilon (TiT3 complex) | TAAGTTGTCCCCCATCC (SEQ ID NO: 37) | 3003 | 0 | 0 | | 0 | 0 | 5 | 28 | 54 |
| CD79A antigen (Ig-associated alpha) | TATGAGGACATCTCCCG (SEQ ID NO: 38) | 79630 | 0 | 2 | | 2 | 2 | 2 | 32 | 20 |
| Pan-leukocyte | | | | | | | | | | |
| CD99 antigen | GGATGTGAAAGGCTGGC (SEQ ID NO: 39) | 283477 | 29 | 52 | | 36 | 31 | 42 | 66 | 60 |
| Monocyte candidate genes | | | | | | | | | | |
| FOS, osteosarcoma viral oncogene homolog | TGGAAAGTGAATTTGAA (SEQ ID NO: 40) | 25647 | 94 (5.5) | 124 | (7.3) | 17 | 21 | 9 | 6 | 4 |
| DUSP1, dual specificity phosphatase 1 | CTTGACATACCTACCAG (SEQ ID NO: 41) | 171695 | 71 (3.0) | 92 | (3.8) | 24 | 17 | 14 | 12 | 2 |
| NFKBIA, NFK gene in B-cell inhibitor, alpha | TAACAGCCAGGAGTGCT (SEQ ID NO: 42) | 81328 | 42 (2.1) | 56 | (2.8) | 20 | 11 | 15 | 16 | 16 |
| ID2, inhibitor of DNA binding 2 | CTAAACTTTTTATAAAA (SEQ ID NO: 43) | 180919 | 33 (1.7) | 42 | (2.2) | 19 | 7 | 5 | 16 | 12 |
| PER1, period homolog 1 | GAGTCCCTGGTGCTGCC (SEQ ID NO: 44) | 445534 | 30 (1.8) | 60 | (3.5) | 17 | 1 | 1 | 0 | 2 |
| SAP30, sin3-associated polypeptide, 30 kDa | TAGAAATGTTCTTTGTG (SEQ ID NO: 45) | 512813 | 10 (1.7) | 30 | (5.0) | 6 | 3 | 4 | 2 | 0 |

Hematopoietic markers and monocyte candidate gene tag counts are tabulated under the various SAGE libraries, along with their associated sequences and gene identification numbers. A total of seven SAGE libraries are shown, five CD14+ monocyte (Monocyte) and two monocyte-depleted (Non-monocyte) libraries. The tag counts shown are normalized to 100,000 tags per library. ( ) represent patient to control C1 tag ratio, P < 0.001. Patient 1 (P1), patient 2 (P2), age-matched control 1 (C1), younger age control 1 (A1), younger age control 2 (A2).

Example 3

Evaluation of Candidate Genes

SAGE tag comparisons were made between the two patients P1 and P2 and the control C1 monocyte SAGE libraries (Table 3). To raise the stringency and reproducibility of the screen, only tags were considered that increased at least 1.5-fold in both P1 and P2 monocyte libraries to obtain a list of 297 candidates (P<0.001, tag sum ≧25) (full list available online). To each tag from this preliminary list the following additional criteria were applied: 1) low tag counts in both control A1 and A2 monocyte libraries to rule out age-related differences; and 2) low tag counts in non-monocyte libraries for selecting relatively monocyte-specific genes.

Using the above criteria, six candidate genes were selected, Finkel-Biskis-Jinkins osteosarcoma gene (FOS), dual specificity phosphatase 1 (DUSP1), nuclear factor of kappa light polypeptide gene enhancer in B cells inhibitor-alpha (NFK-BIA), inhibitor of DNA binding 2 (ID2), period homolog 1 (PER1) and sin 3-associated polypeptide (SAP30), all associated with regulatory or transcriptional functions (Table 3). The two most differentially expressed candidates were FOS, a proto-oncogene involved in proliferation and differentiation, and DUSP1, a stress response phosphatase important for mitogen-activated protein kinase (MAPK) regulation (Shaulian et al., *Nat Cell Biol* 4(5):E131-136, 2002; Clark et al., *J Endocrinol* 178(1):5-12, 2003; Farooq et al., *Cell Signal* 16(7):769-779, 2004). A few differentially expressed SAGE tags were without gene assignment, and follow up of these revealed that they are polymorphic tags from highly expressed known genes. No strong differentially expressed candidates were observed between the non-monocyte SAGE libraries P1 and A1 that contained mixed populations of cells.

Figure 4:
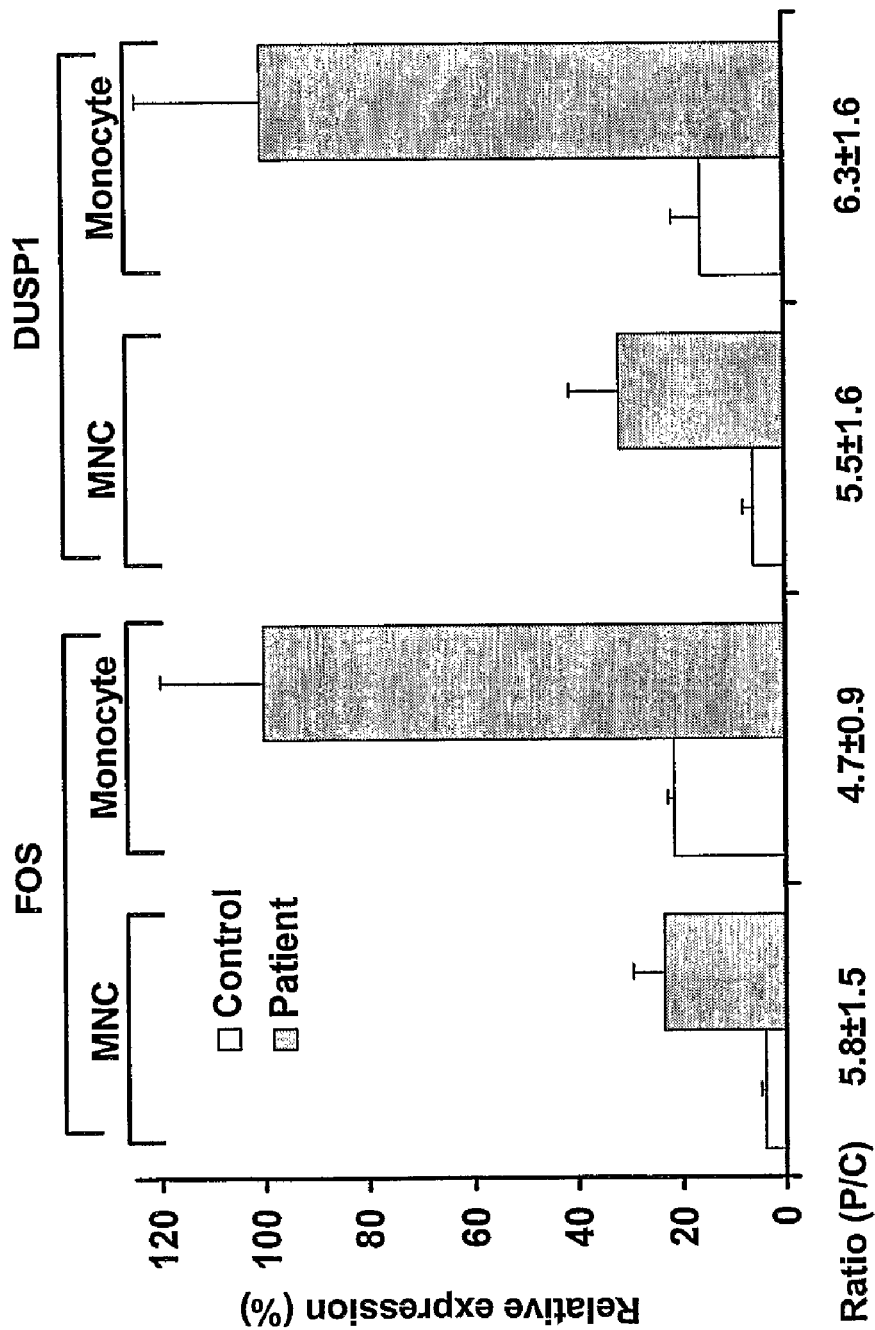
FIG. 4 is a bar graph of FOS and DUSP1 fold change ratios in patients compared to controls (Ratio (P/C)) are preserved whether whole mononuclear cells (MNC) or purified monocytes (Monocyte) are used for RT-PCR. Values shown as mean±SE, n=6, for patients and controls.

To minimize sample processing and purification requirements, the feasibility of using whole mononuclear cell (MNC) fractions for measuring monocyte-specific gene expression was examined. This appeared possible because the monocyte content of patient and control MNC samples were similar, 20±9% and 22±9%, respectively. The fold changes of FOS and DUSP1 between patients and controls using MNCs was determined and compared to those obtained using purified monocytes. The fold change ratios obtained by using either MNC or monocyte fractions were almost identical, indicating that MNCs could be used to accurately detect monocyte-specific gene expression (FIG. 4). It is noteworthy that MNC RT-PCR values indirectly reflected monocyte content (approx. 20%) and that the purification of monocytes using CD14 antibody did not significantly alter FOS or DUSP1 gene expression ratios.

Example 4

Quantitative RT-PCR of Subject Samples

To prospectively confirm differential gene expression in circulating monocyte using MNCs, a total of 25 patients scheduled for CEA and 19 age-matched normal control subjects were selected for our study (Table 1). Though the patient and control subjects were closely matched by age, notable differences could be seen due to the inherent risk factors associated with atherosclerosis such as male gender, family history and prior history of coronary artery disease. Treatment for hypertension and hyperlipidemia were more prevalent among the patients compared to controls, 92% versus 32% and 80% versus 37%, respectively. However, the blood pressure and LDL cholesterol levels were comparable between the two groups at the time of the study.

Figure 1B:
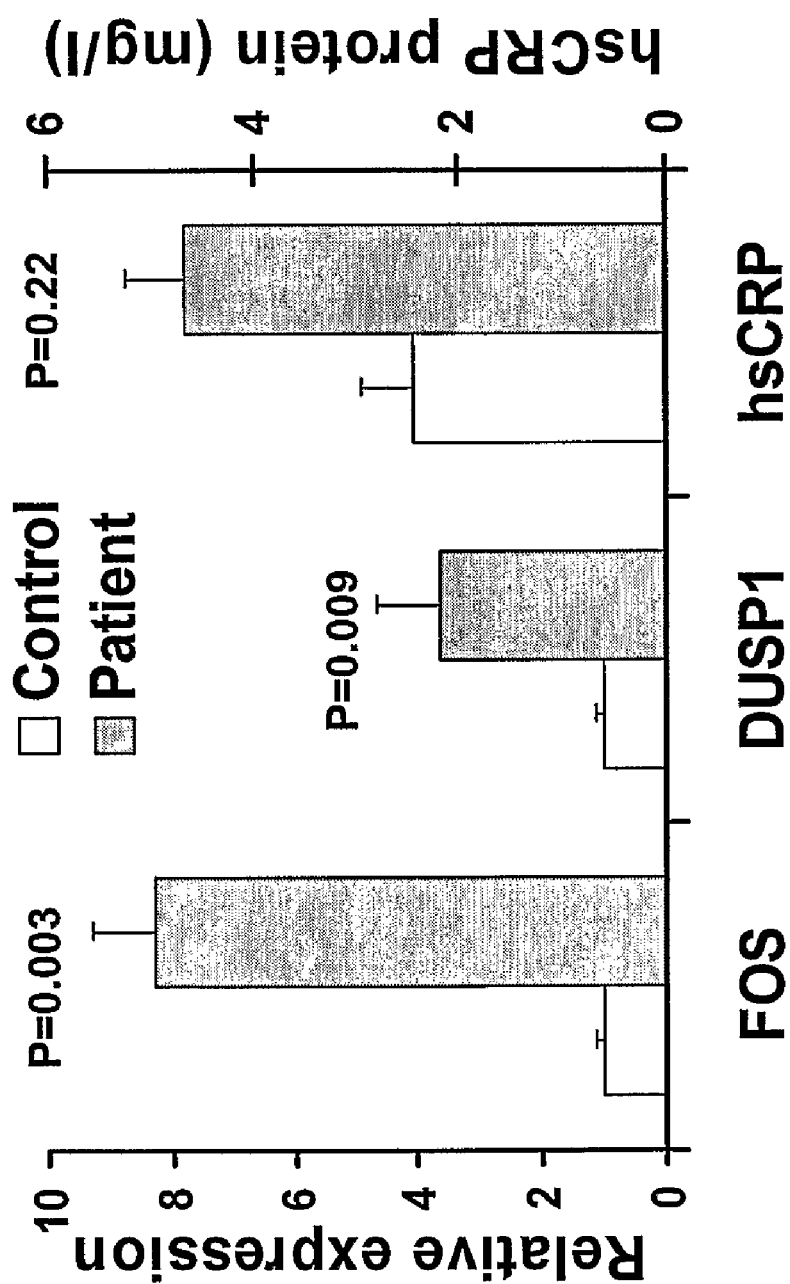
Figure 1C:
Figure 1D:
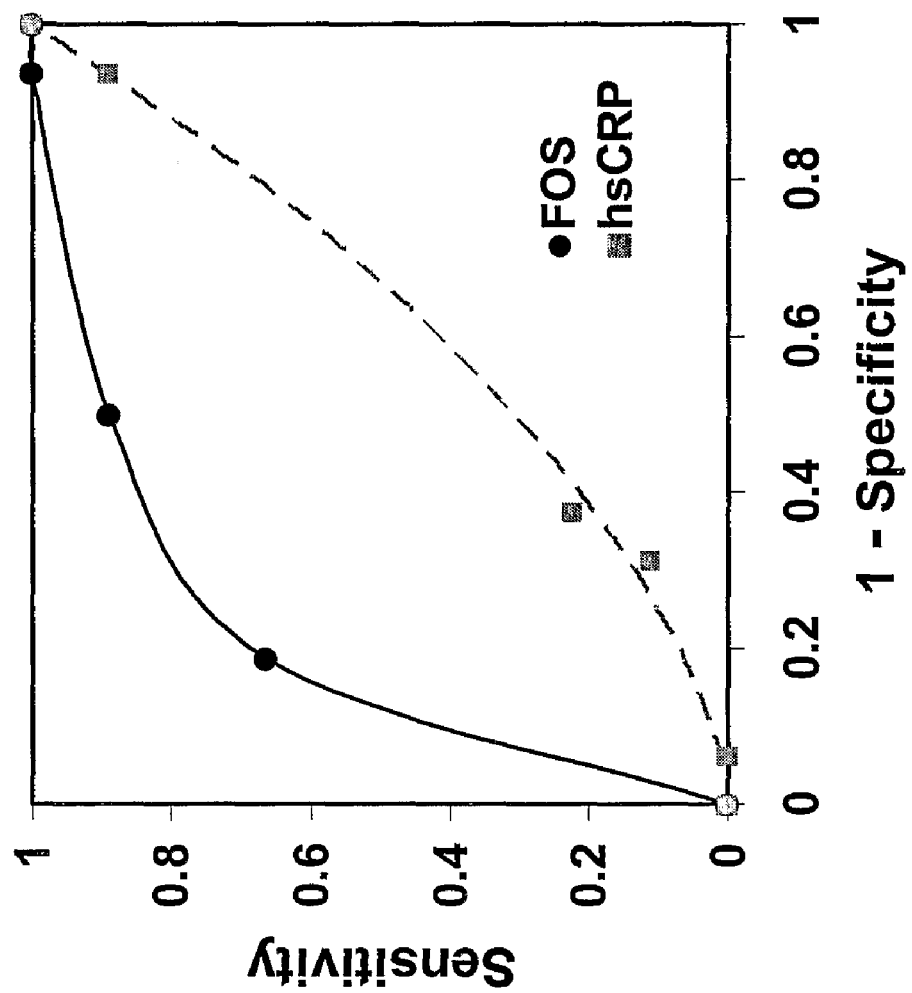
Figure 1E:
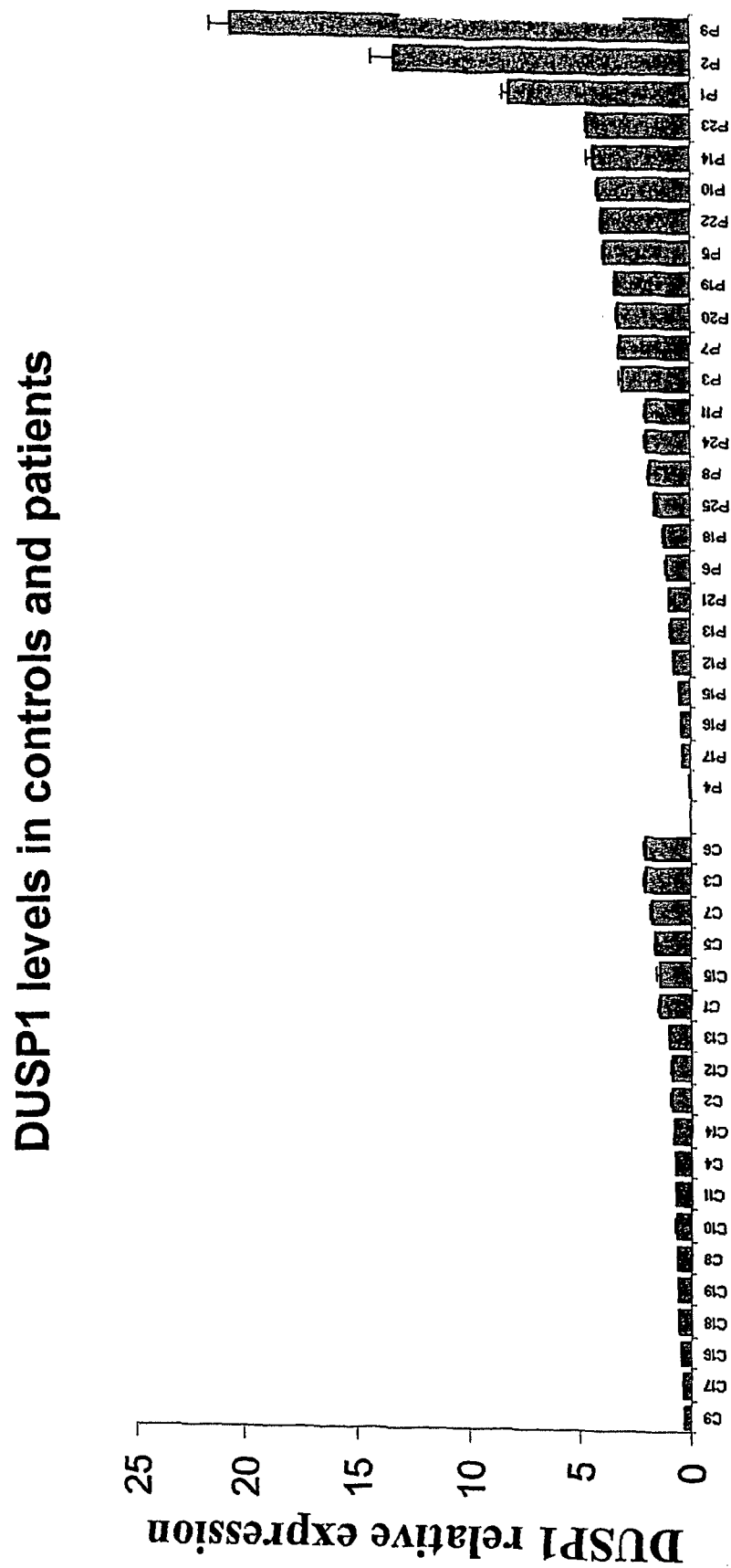

The relative expression levels of the six candidate genes were color-coded and ordered by their average values (AVG) for the control and patient groups (FIG. 1A). FOS and DUSP1 had the highest expression pattern in patients confirming their SAGE tag counts, and they largely determined the ordering of the patients. The mean FOS and DUSP1 RT-PCR fold increase in patients over controls were 8.3±2.2 (P=0.003) and 3.6±0.9 (P=0.009), respectively (FIG. 1B). In the follow up studies, FOS gave the most consistent difference between patients and controls. FIGS. 1C and 1E show individual control and patient subject RT-PCR levels of FOS and DUSP1, respectively. There was a high degree of correlation between FOS and DUSP1 levels.

Example 5

Clinical Significance of Increased FOS Level

Because plasma hsCRP has been shown to be a clinically useful indicator of inflammation and predictor of future cardiac events, it was tested as to whether FOS might be similarly diagnostic. In comparison to FOS, hsCRP was not as significantly elevated in patients versus control subjects at 1.9±0.2 fold (P=0.22) (FIG. 1B). The correlation between hsCRP and FOS levels was low (correlation coefficient <0.6). Plasma interleukin-6 level, another inflammatory marker, was measured, but it too did not show as marked a difference as FOS.

In order to determine whether there were any differences among the patients that could account for the variations in FOS levels, all available patient information such as CEA surgical outcome (3 months to over one year follow up), cardiac risk factors, associated medical conditions and medications, as well as quantitative measures such as body mass index (BMI) and 10-year Framingham cardiac risk, were examined (Table 1). The large number of variables in a limited patient population did not allow a controlled multivariate analysis for FOS levels. Surprisingly, given that all patients had peripheral vascular disease as evidenced by their need for CEA surgery, it was observed that previous history of coronary revascularization (coronary artery bypass graft surgery or angioplasty) appeared to associate with elevated FOS level (FIG. 1C). Empirically taking the highest control subject's FOS level as the threshold for a positive test, eight out of the nine coronary revascularization patients were detected (89% sensitivity). The average (AVG) RT-PCR values of the combined top six candidates did not improve the sensitivity. The receiver operating characteristic (ROC) for FOS at identifying coronary revascularization patients revealed sensitivities and specificities that were higher than for hsCRP (FIG. 1D).

Figure 6:
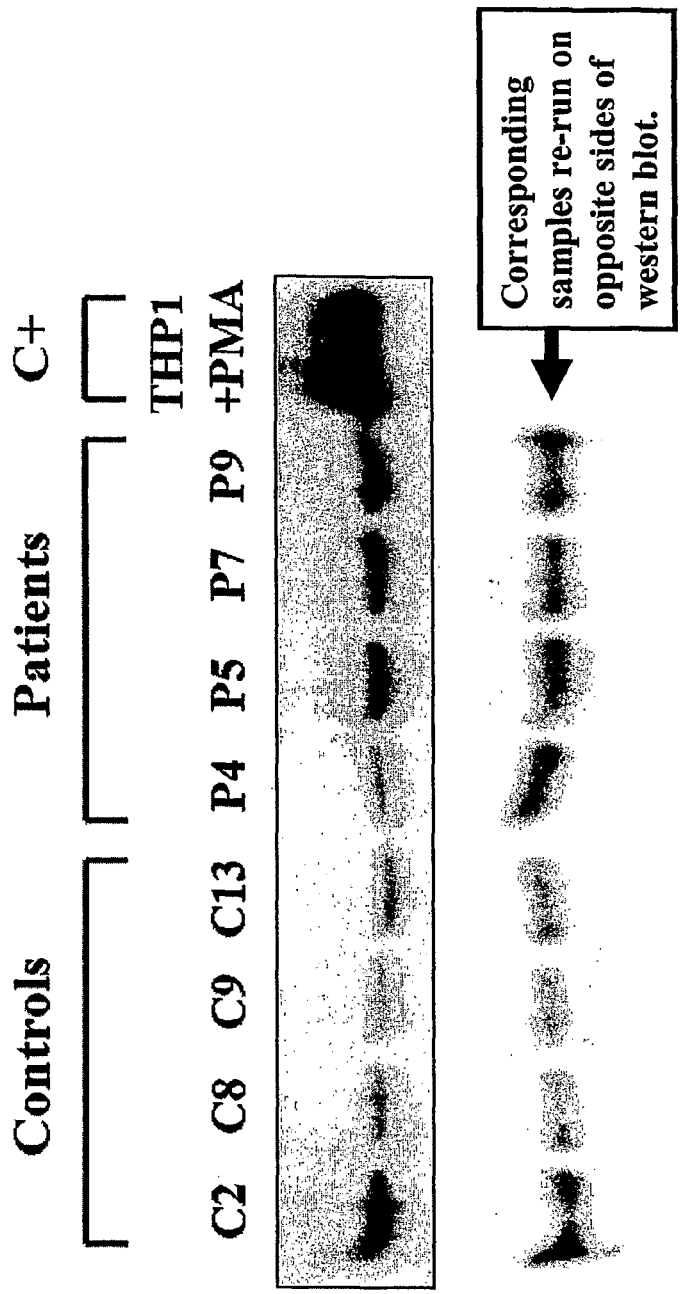
FIG. 6 is a digital image of FOS protein expression in plasma. It shows a Western blot using anti-FOS antibody on equal amounts of four controls and four patients' plasma protein (50 micrograms). As positive control for FOS protein, THP1 cells were stimulated with PMA (C+). The two lower panels for controls and patients show the same corresponding samples re-run on opposite sides of the gel to control for potential differences in transfer efficiency of proteins in different areas of the gel.

A similar observation was made for DUSP1 as for FOS (FIG. 1E). Patients with more extensive atherosclerosis as evidenced by previous history of coronary revascularization were also identified by higher levels of DUSP1. Protein levels of FOS in Patient and Control plasma samples were examined by Western blot analysis using anti-FOs antibody (FIG. 6). Higher levels of FOS were detected, although the level was not as significantly elevated as for FOS mRNA. These observations demonstrate that the optimization of immuno-spectrophotometric assays may dramatically simplify the measurement of FOS expression in patients.

Example 6

Expression of FOS in Plaques and Atherosclerosis Models

Figure 2A:
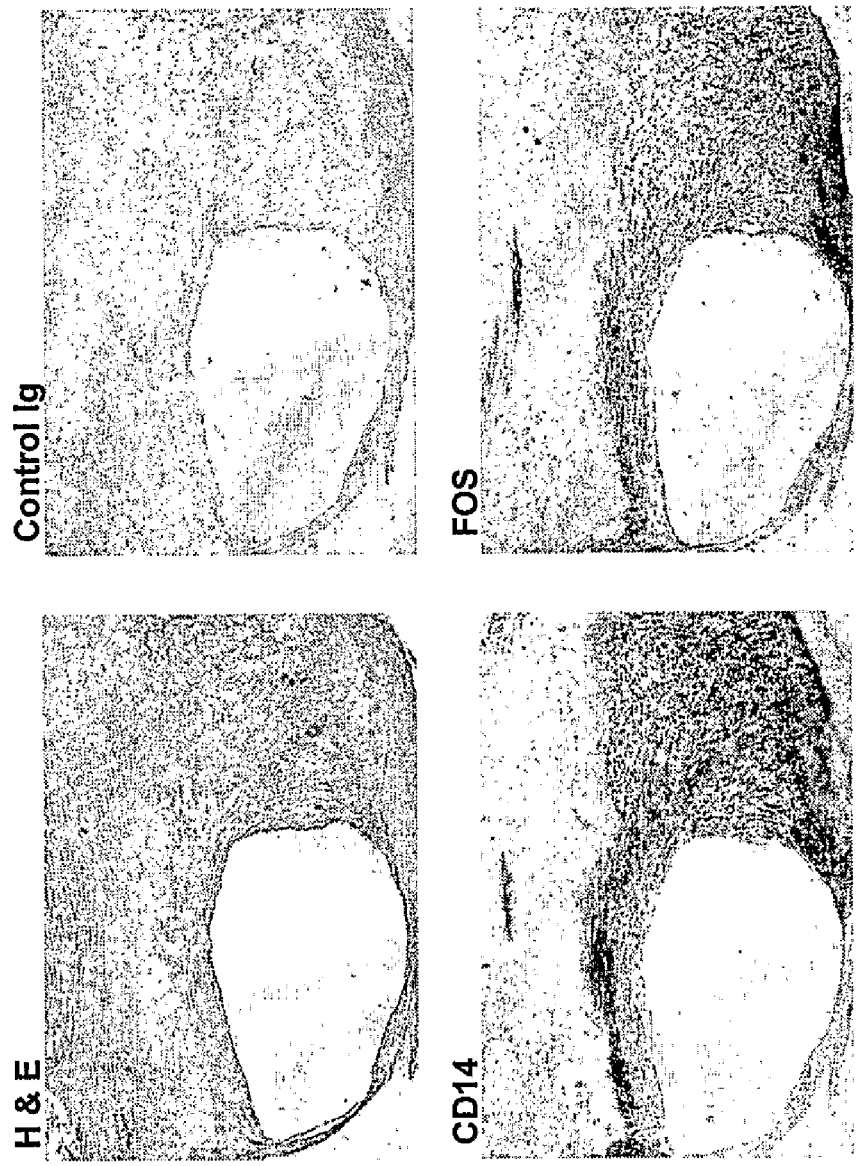
FIGS. 2A-2D are digital images and graphs showing expression of FOS in human carotid plaque macrophages and in activated human monocytic cells and ApoE KO mouse splenocytes.
Figure 5A:
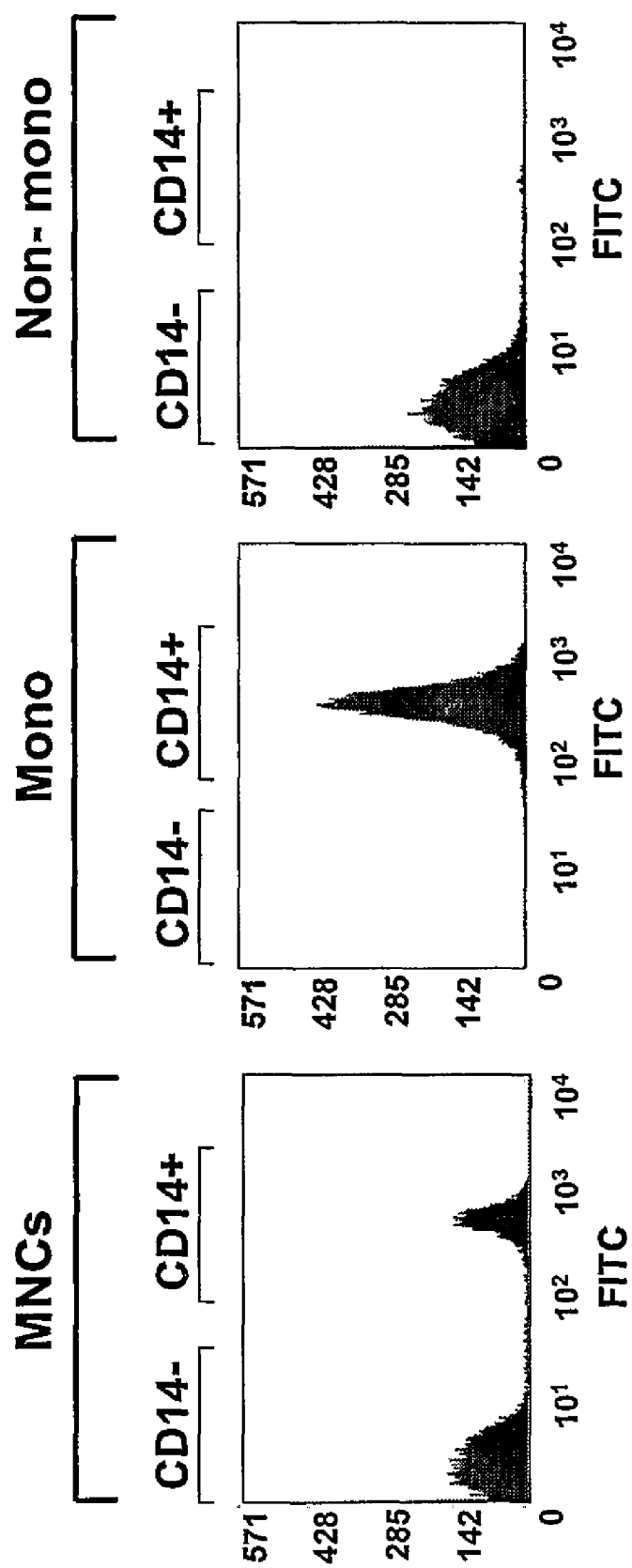
FIGS. 5A-5B are a set of plots and digital images showing the confirmation of monocyte and macrophage purity.
Figure 5B:
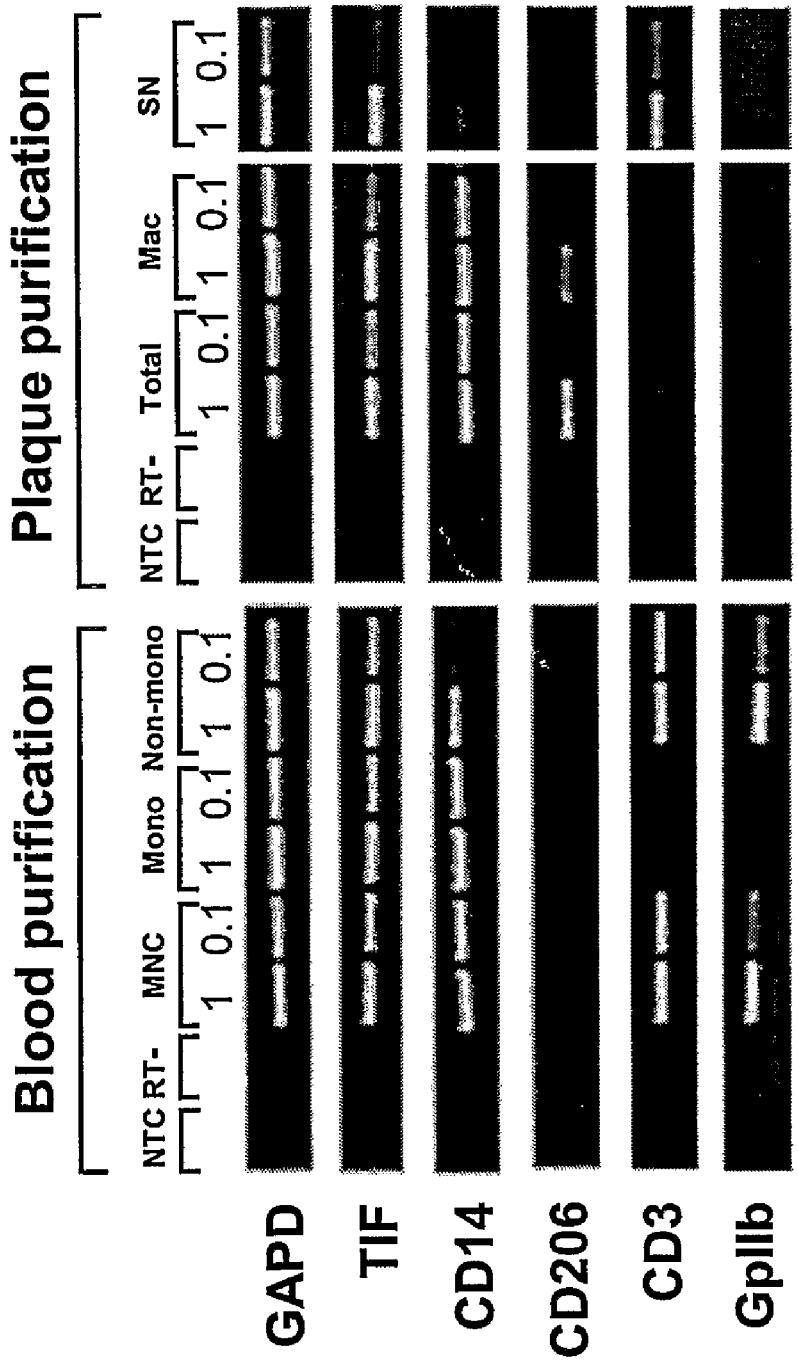

It was questioned whether candidate genes involved in pathogenesis should be expressed and upregulated in atherosclerotic plaque macrophages. As a first step, immunohistochemistry was performed on serial sections of CEA plaques and observed specific colocalization of FOS to CD14+ cells (FIG. 2A). To ascertain FOS expression in macrophages, CD14+ cells were purified from a number of carotid plaques and verified macrophage enrichment using RT-PCR (FIG. 5B). Progressively higher levels of the six candidate genes were observed in MNCs, monocytes (Mono) and plaque macrophages (Mac), respectively, supporting the hypothesis disclosed herein (FIG. 5B). The highest levels were observed for the top two circulating monocyte candidates FOS and DUSP1.

Figure 2C:
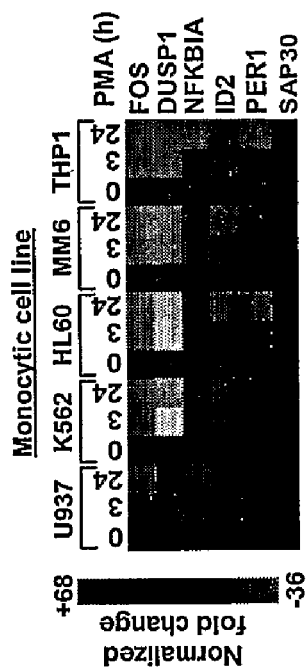
Figure 2B:
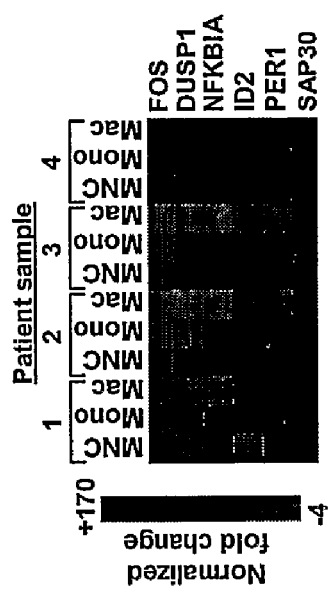

To further establish the biological significance of these candidate genes, their expression was examined in several different monocytic cell lines stimulated by phorbol 12-myristate 13-acetate (PMA), a potent stimulus for differentiating monocytes into macrophage-like cells. As early as 3 hours after PMA treatment, there was induction of the candidate genes. DUSP1 was repressed in two of the cell lines, but FOS was uniformly induced in all five cell lines validating it was the preferable indicator of monocyte activation (FIG. 2C).

Figure 2D:
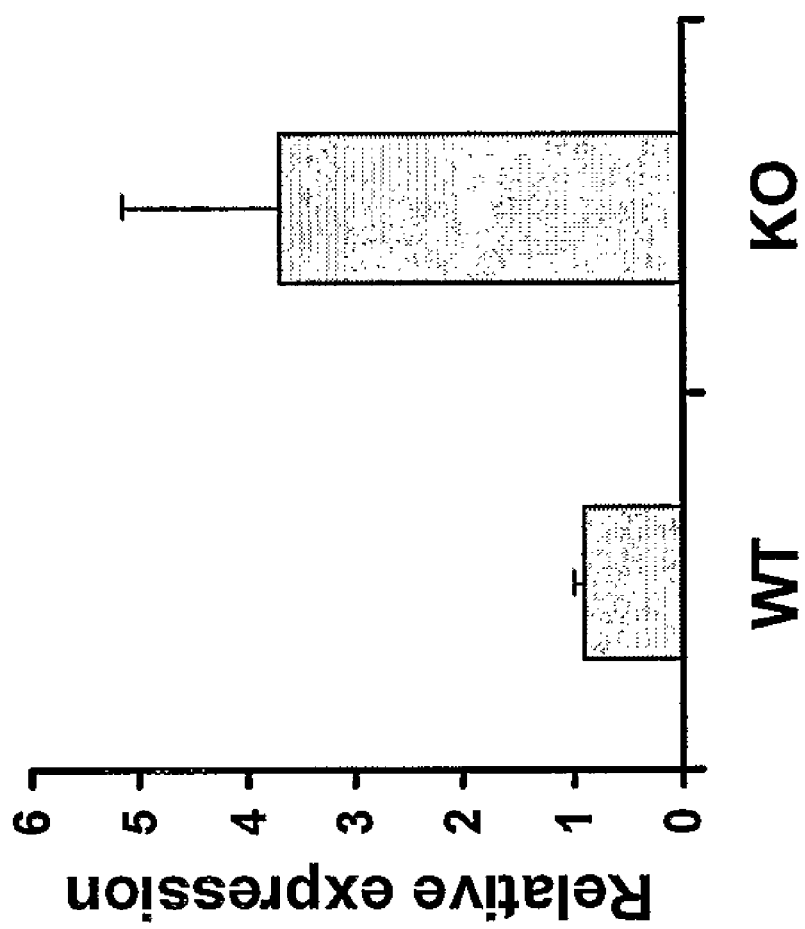

To address whether FOS might be involved in the development of atherosclerosis, its level was examined in splenocytes representing circulating hematopoietic cells from ApoE gene wild-type (WT) and knockout (KO) mice by RT-PCR. The KO mice develop spontaneous aortic atherosclerotic plaques to varying degrees. As with the patient mononuclear cells, there was a range of FOS induction in KO mice but the mean value was significantly higher than in WT littermates (FIG. 2D).

Example 7

Modulation of FOS Affects Monocyte Function

Figure 3B:
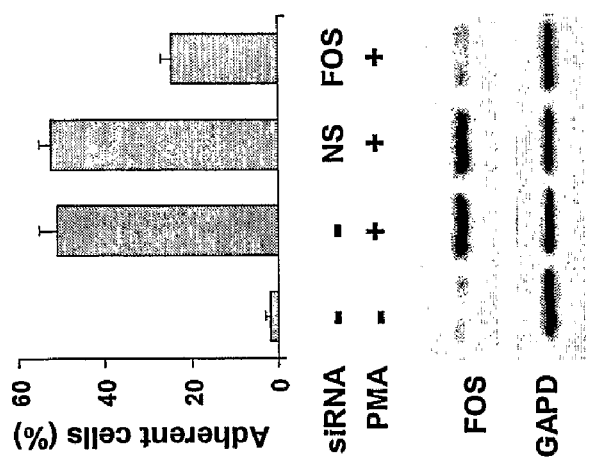
FIGS. 3A-3B are digital images and graphs showing the functional effects of statin and FOS siRNA inhibition on monocyte activation by PMA.
Figure 3A:
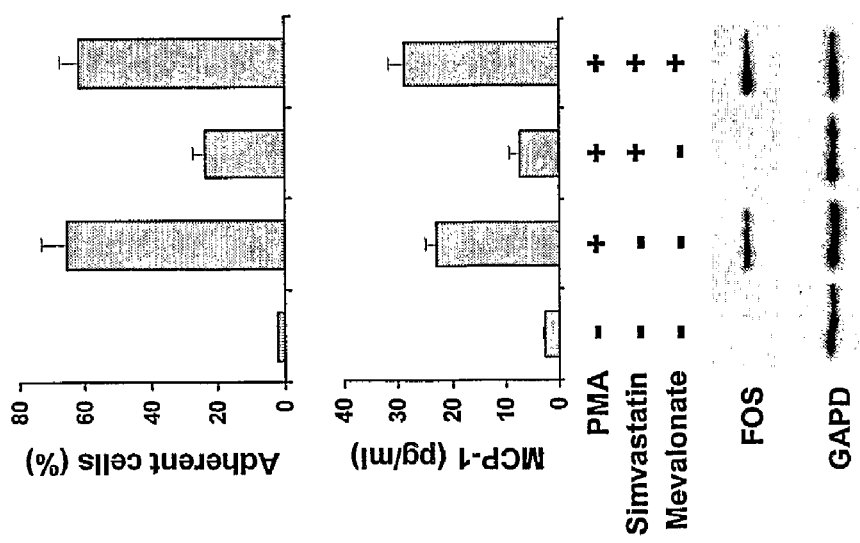

The efficacy of statins in both the primary and secondary prevention of atherosclerosis has been firmly established and are now an integral part of treatment against disease progression. Using THP1 cells stimulated with PMA as an in vitro model, the effect of statins was examined on FOS expression and two important functions associated with monocyte activation, adhesion and release of monocyte chemoattractant protein 1 (MCP-1), a critical component of atherosclerotic plaque formation (Gu et al., *Mol Cell* 2(2):275-281, 1998; Boring et al., *Nature* 394(6696):894-897, 1998). Pretreatment with statins prior to stimulation with PMA reduced the levels of FOS protein (FIG. 3A). This reduction in FOS was reversed by the addition of mevalonate, the product of statin-inhibited HMG-CoA reductase, demonstrating pharmacologic specificity. In parallel with FOS reduction, there was an approximately 70% reduction in monocyte adhesion to plastic substratum and MCP-1 release into medium compared to control (FIG. 3A). Both of these functional observations associated with statin treatment were specifically reversed by including mevalonate in the medium.

In addition to pharmacologic inhibition of FOS, the genetic inhibition of FOS transcripts was examined using small interfering RNA (siRNA) molecules. FOS-specific siRNA transfection markedly reduced the induction of FOS protein after 4 hours of PMA treatment as assessed by Western-blotting (FIG. 3B). In association with the reduction in FOS protein induction, PMA-stimulated monocyte adhesion was decreased by about 50% during this same time period. In contrast, siRNA directed toward nonspecific sequences (NS) did not have any inhibitory effect on either FOS protein level or cellular adhesion.

The present examples demonstrate the utility of focusing on the in vivo transcriptome of readily available cells involved in an important disease process. Using the SAGE technique, six regulatory genes were identified that were highly expressed in the monocytes of patients with atherosclerosis. Among the candidates genes, FOS was the most differentially expressed marker fitting. Both the cross-species conservation of FOS expression in atherosclerosis models and its role in monocyte activation highlight its importance in disease pathogenesis.

In comparison to control subjects, FOS transcript levels were increased over eight-fold in patients requiring carotid artery endarterectomy for atherosclerotic stenosis. Compared to plasma hsCRP, FOS transcript levels in the studies presented herein were more sensitive to disease severity. The only coronary revascularization patient missed by FOS levels was one of three patients on maximum statin doses, all of whom also had low FOS levels. Finally, out of the 25 patients enrolled in this study, one patient had an ischemic event on follow up. Nine months after the CEA surgery, the patient with the highest FOS level (P9) had subsequent thrombosis of a prior femoral artery bypass graft requiring emergent revascularization. Though this patient did not have prior coronary revascularization, she had a known 90% stenosis of the right coronary artery and was not on statin treatment. It is also noteworthy that control subjects on statin treatment had lower levels of FOS though the sample number is limited.

The disclosed data demonstrates functional inhibition of monocyte activation correlates with statin treatment. Recently, the PROVE IT-TIMI 22 clinical trial showed significant benefit of high-dose over standard-dose statin treatment in acute coronary syndrome patients (Cannon et al., *N Engl J Med* 350(15):1495-1504, 2004). The combination of the results of this clinical trial with the expression data presented herein demonstrates that monocytes can be used to test therapeutic regimens to determine if they are of use in treating atherosclerosis. In one example, a peripheral blood sample from a patient can be used to determine if a therapeutic protocol would be beneficial to that individual subject. In another example, a monocyte cell line can be used to determine if a therapeutic agent could be of use generally in treating atherosclerosis.

A simplified RT-PCR test using whole mononuclear cell fractions is presented herein. However, any sensitive and specific FOS assay and/or DUSP1 assay can be developed and performed. Without being bound by theory, FOS is known to be a reactive transcriptional regulator, and this could be the reason that it is useful as a monitor of disease activity or even treatment efficacy. The digital and quantitative nature of the SAGE database allows monocyte and non-monocyte transcriptomes to be available online to all investigators. These transcriptomes can be used to identify other genes of use in detecting atherosclerosis, determining the prognosis of a specific subject, or screening for agents of use in treating atherosclerosis. FOS expression (which is important for cell differentiation) is believe to be useful as an early indicator of coronary calcification, the molecular equivalent of coronary artery calcium scores that are used for coronary artery disease screening (see O'Rourke et al., *J Am Coll Cardiol* 36(1):326-340, 2000).

It will be apparent that the precise details of the methods or compositions described may be varied or modified without departing from the spirit of the described invention. We claim all such modifications and variations that fall within the scope and spirit of the claims below.

The invention claimed is:

1. A method of detecting the presence or absence of atherosclerosis or determining the severity of atherosclerosis in a subject, comprising
    (a) assaying the expression of Finkel-Biskis-Jinkins osteosarcoma (FOS), Dual specificity phosphatase 1 (DUSP1), or both FOS and DUSP1 in peripheral blood monocytes in a biological sample from the subject; or,
    (b) assaying the expression of FOS protein in a biological sample of plasma from the subject;
    wherein either (a) an increase in the expression of FOS, DUSP1, or both FOS and DUSP1 in the peripheral blood monocytes in the biological sample as compared to a control or (b) an increase in FOS protein in the biological sample of plasma as compared to a control detects the presence of atherosclerosis in the subject or determines the severity of atherosclerosis in the subject.

2. The method of claim 1, wherein the method determines the presence or absence of atherosclerosis in the subject.

3. The method of claim 1, wherein the method determines the severity of atherosclerosis in the subject.

4. The method of claim 1, wherein the control is a standard value of a level of expression in one or more subjects known not to have atherosclerosis.

5. The method of claim 1, wherein the method comprises assaying the expression of FOS, DUSP1, or both FOS and DUSP1 in peripheral blood monocytes by assessing the presence or absence of FOS mRNA, DUSP1 mRNA, or both FOS and DUSP1 mRNA.

6. The method of claim 5, wherein assaying the presence or absence of FOS mRNA, DUSP1 mRNA, or both FOS and DUSP1 mRNA comprises a polymerase chain reaction or a hybridization reaction.

7. The method of claim 6, wherein assaying the presence or absence of FOS mRNA, DUSP1 mRNA, or both FOS and DUSP1 mRNA comprises reverse transcriptase polymerase chain reaction (RT-PCR).

8. The method of claim 1, wherein the method comprises assaying the expression of FOS, DUSP1, or both FOS and DUSP1 in peripheral blood monocytes assessing the presence or absence of FOS protein, DUSP1 protein, or both FOS protein and DUSP1 protein.

9. The method of claim 8, wherein assaying the presence or absence of FOS protein, DUSP1 protein, or both FOS protein and DUSP1 protein comprises contacting the monocytes or a component thereof with an antibody that specifically binds FOS protein, an antibody that specifically binds DUSP1 protein, or an antibody that binds FOS protein and an antibody that binds DUSP1 protein.

10. The method of claim 9, wherein the antibody that specifically binds FOS protein, the antibody that specifically binds DUSP1 protein, or the antibody that binds FOS protein and the antibody that binds DUSP1 protein are directly labeled.

11. The method of claim 10, wherein the label is a radioactive marker, a fluorescent marker, an enzyme or a metal.

12. The method of claim 8, wherein assessing the expression of FOS protein, DUSP1 protein, or both FOS and DUSP1 protein comprises mass spectrometry.

13. The method of claim 1, wherein the method comprises assaying the expression of FOS, DUSP1, or FOS and DUSP1 in peripheral blood monocytes in a biological sample from the subject.

14. The method of claim 13, wherein the method comprises assaying the expression of FOS in peripheral blood monocytes in a biological sample from the subject.

15. The method of claim 14, wherein assaying the expression of FOS in peripheral blood monocytes comprises assaying the presence or absence of FOS mRNA.

16. The method of claim 14, wherein assaying the expression of FOS in peripheral blood monocytes comprises assaying the presence or absence of FOS protein.

17. The method of claim 13, wherein the method comprises assaying the expression of DUSP1 in peripheral blood monocytes in a biological sample from the subject.

18. The method of claim 17, wherein assaying the expression of DUSP1 in peripheral blood monocytes comprises assaying the presence or absence of DUSP1 mRNA.

19. The method of claim 17, wherein assaying the expression of DUSP1 in peripheral blood monocytes comprises assessing the presence or absence of DUSP1 protein.

20. A method of diagnosing atherosclerosis or determining the severity of atherosclerosis in a subject, comprising
assaying the expression of Finkel-Biskis-Jinkins osteosarcoma (FOS) protein in a biological sample of plasma from the subject;
wherein an increase the expression of FOS protein in the biological sample of plasma as compared to a control indicates that the subject has atherosclerosis or indicates the severity of atherosclerosis in the subject.

21. The method of claim 20, wherein assaying the expression of FOS protein, comprises assaying the presence or absence of FOS protein.

22. The method of claim 21, wherein assaying the presence or absence of FOS protein comprises contacting the plasma with an antibody that specifically binds FOS.

23. The method of claim 22, wherein the antibody that specifically binds FOS protein is directly labeled.

24. The method of claim 23, wherein the label is a radioactive marker, a fluorescent marker, an enzyme or a metal.

25. The method of claim 21, wherein assessing the expression of FOS protein comprises mass spectrometry.

26. The method of claim 20, wherein the method comprises assaying the expression of FOS protein in a biological sample of plasma from the subject using an enzyme-linked immunosorbent assay, a radioimmunoassay, Western blotting, fluorimetric detection or mass spectrometry.

27. The method of claim 26, wherein the method comprises contacting the plasma with an antibody that specifically binds the FOS protein.

28. The method of claim 27, wherein the antibody that specifically binds the FOS protein is directly labeled.

29. The method of claim 28, wherein the label is a radioactive marker, a fluorescent marker, an enzyme or a metal.

30. The method of claim 26, wherein assaying the expression of FOS protein in a biological sample of plasma from the subject comprises mass spectrometry.

* * * * *

UNITED STATES PATENT AND TRADEMARK OFFICE
CERTIFICATE OF CORRECTION

| | | |
|---|---|---|
| PATENT NO. | : 7,998,682 B2 | Page 1 of 2 |
| APPLICATION NO. | : 11/661714 | |
| DATED | : August 16, 2011 | |
| INVENTOR(S) | : Hwang et al. | |

It is certified that error appears in the above-identified patent and that said Letters Patent is hereby corrected as shown below:

<u>On the Title Page, Item (56) OTHER PUBLICATIONS:</u>
Page 2, right column, at Patino et al., "atheroscleorosis," should read --atherosclerosis,--.

<u>On the Title Page, Item (57) ABSTRACT:</u>
Page 1, right column, "An increase the expression" should read --An increase in the expression--.

Page 1, right column, "decrease the expression of FOS," should read --decrease in the expression of FOS--.

<u>In the Specification:</u>
Column 2, line 30, "FOS and or DUSP1" should read --FOS and/or DUSP1--.
Column 2, lines 35-36, "in a monocytes" should read --in monocytes--.
Column 3, line 27, "membrance" should read --membrane--.
Column 4, line 60, "SEQ ID NOs: 23-34" should read --SEQ ID NOs: 23-24--.
Column 6, line 6, "can changed" should read --can be changed--.
Column 6, line 29, "ateriosclerosis" should read --arteriosclerosis--.
Column 7, line 52, "(Feb. 23, 2996)," should read --(Feb. 23, 1996),--.
Column 7, line 55, "Orthogs" should read --Orthologs--.
Column 8, line 12, "Orthogs" should read --Orthologs--.
Column 8, line 35, "B cell" should read --B cells--.
Column 9, line 57, "proteins  Nucleic" should read --proteins. Nucleic--.
Column 10, line 51, "amounts a" should read --amounts of a--.
Column 10, line 59, "amount of can" should read --amount can--.

Signed and Sealed this
Twenty-ninth Day of May, 2012

David J. Kappos
*Director of the United States Patent and Trademark Office*

CERTIFICATE OF CORRECTION (continued)
U.S. Pat. No. 7,998,682 B2

Column 11, line 9, "such a sign," should read --such as a sign,--.

Column 13, lines 63-64, "subject with known not be have" should read --subject known not to have--.

Column 13, line 64, "and to at low" should read --and to be at low--.

Column 17, line 8, "pBluscript" should read --pBluescript--.

Column 18, line 4, "calorimetric" should read --colorimetric--.

Column 18, line 41, "In a one" should read --In one--.

Column 19, line 8, "florescence" should read --fluorescence--.

Column 19, line 50, "several embodiment," should read --several embodiments,--.

Column 19, line 53, "prepared to a control." should read --compared to a control.--.

Column 19, line 61, "subject with known not be have" should read --subject known not to have--.

Column 19, line 62, "at low risk" should read --be at low risk--.

Column 20, line 28, "FOS and or the" should read --FOS and/or the--.

Column 22, line 30, "subject with known not be have" should read --subject known not to have--.

Column 22, line 31, "to at low risk" should read --to be at low risk--.

Column 22, line 41, "buffer" should read --buffer.--.

Column 25, lines 8-9, "compared the results" should read --compared to the results--.

Column 25, line 36, "material and methods" should read --materials and methods--.

Column 26, line 7, "Bichemical" should read --Biochemical--.

Column 26, line 44, "lystates" should read --lysates--.

Column 26, line 66, "2004)." should read --2004)).--.

Column 27, TABLE 1, third column, "(SEQ ID NO: 20" should read --(SEQ ID NO: 20)--.

Column 27, TABLE 1, third column, "(SEQ ID NO: 24" should read --(SEQ ID NO: 24)--.

Column 30, line 6, "PCR RT-PCR)" should read --PCR (RT-PCR)--.

Column 30, TABLE 3, second column, "TGGTGCAGCGCCCTGAA" should read --TGGTCCAGCGCCCTGAA--.

Column 33, line 11, "monocyte" should read --monocytes--.

Column 34, line 11, "anti-FOs antibody" should read --anti-FOS antibody--.

Column 36, line 35, "is believe to" should read --is believed to--.

Column 50, claim 20, "increase the" should read --increase in the--.

Column 50, claim 21, "protein, comprises" should read --protein comprises--.